United States Patent [19]
Kozak

[11] Patent Number: 6,077,837
[45] Date of Patent: Jun. 20, 2000

[54] PRODRUGS WITH ENHANCED PENETRATION INTO CELLS

[75] Inventor: Alexander Kozak, Rehovat, Israel

[73] Assignee: D-Pharm Ltd., Rehovat, Israel

[21] Appl. No.: 09/178,210

[22] Filed: Oct. 23, 1998

Related U.S. Application Data

[62] Continuation of application No. 08/479,959, Jun. 7, 1995, which is a continuation-in-part of application No. 08/481,243, filed as application No. PCT/GB94/00669, Aug. 21, 1995, Pat. No. 5,985,854.

[51] Int. Cl.$^7$ .................................................. A61K 31/685
[52] U.S. Cl. ........................ 514/77; 514/76; 514/114; 514/117; 514/143; 514/144; 514/826; 554/78; 554/79; 554/80
[58] Field of Search ....................... 54/76, 77, 114, 54/117, 143, 144, 826; 551/78, 79, 80

[56] References Cited

U.S. PATENT DOCUMENTS

| 5,149,794 | 9/1992 | Yatvin et al. |
| 5,227,514 | 7/1993 | Meul et al. |

FOREIGN PATENT DOCUMENTS

| 0275005 | 7/1988 | European Pat. Off. |
| 0325160 | 7/1989 | European Pat. Off. |
| 3133987 | 6/1991 | Japan |
| 679856 | 4/1992 | Switzerland |
| 8905358 | 6/1989 | WIPO |
| 9000555 | 1/1990 | WIPO |
| 9010448 | 9/1990 | WIPO |
| 9116920 | 11/1991 | WIPO |
| 9300910 | 1/1993 | WIPO |
| 9408573 | 4/1994 | WIPO |

OTHER PUBLICATIONS

NITS Technical Notes, No. 9, 1984, "Prodrugs based on phpospholipid–nucleoside conjugates" Springfield, VA, p. 630.

Stuttgart, DE, Geb. 1992; European J. of Pharmaceutics and Biopharmaceutics, 38(1):1–6. O. Vaizoglu et al., Jul. 26, 1989, EP–A–0325 160 (Hoechst A.G.).

Hostetler et al., Jun. 1991, "Phosphatidylaazothymidine. Mechanism of antiretroviral action in cem cells." J. Biol. Chem. 266(18):11714–11715.

Gusovsky et al., Feb. 1990, "Mechanism of maitotoxin-stimulated phosphoinostitide breakdown in HL–60 cells." J. Pharmacol. Ex. Ther. 252(2):469–470.

Govez–Cambronero et al., Apr. 1991, "Platelet activating factor induces tyrosine phosssphorylation in human neutrophils." J. Biol. Chem. 266(10):6240–5, 1993.

Natarajan et al. "Activation of endothelial cell phospholipase D by hydrogen peroxide and fatty acid hydroperoxide." J.Biol. Chem 268(2):930–7., 1994.

Coorssen et al., "GTP.gamma.S and phorbol ester act synergistically to stimulate both calcium independent secretion and phospholipase D activity in permeabilized human platertis. Inhibition by BAPTA and analogs" FEBS Lett. 316(2):170–4, 1997.

Duan et al., Feb. 1994, "Conversion to CA(2+)–independent form of Ca2+/calmodulin protein kinase II in rat pancreatic acini." Biochem. Biophys. Res. Commun. 199(1):368–373.

*Primary Examiner*—Deborah D. Carr
*Attorney, Agent, or Firm*—Davidson, Davidson & Kappel, LLC.

[57] ABSTRACT

The invention relates to a pharmaceutically acceptable prodrug which is a covalent conjugate of a pharmacologically active compound and an intracellular transporting adjuvant, characterized by the presence of a covalent bond which is scission-sensitive to intracellular enzyme activity. The prodrug may be used in a technique for treating a condition or disease in a mammal related to supranormal intracellular enzyme activity, whereby on administering it to a human having such condition or disease, the bond is broken in response to such activity, and the pharmacologically active compound is activated selectively within cells having such supranormal intracellular enzyme activity.

21 Claims, 8 Drawing Sheets

PRODRUG EFFECT IN PERMANENT PARTIAL GLOBAL BRAIN ISCHEMIA

EFFECT OF PRODRUG ON FREE CALCIUM LEVEL IN HUMAN LYMPHOCYTES

EFFECT OF PRODRUG ON FREE CALCIUM LEVEL IN HUMAN LYMPHOCYTES

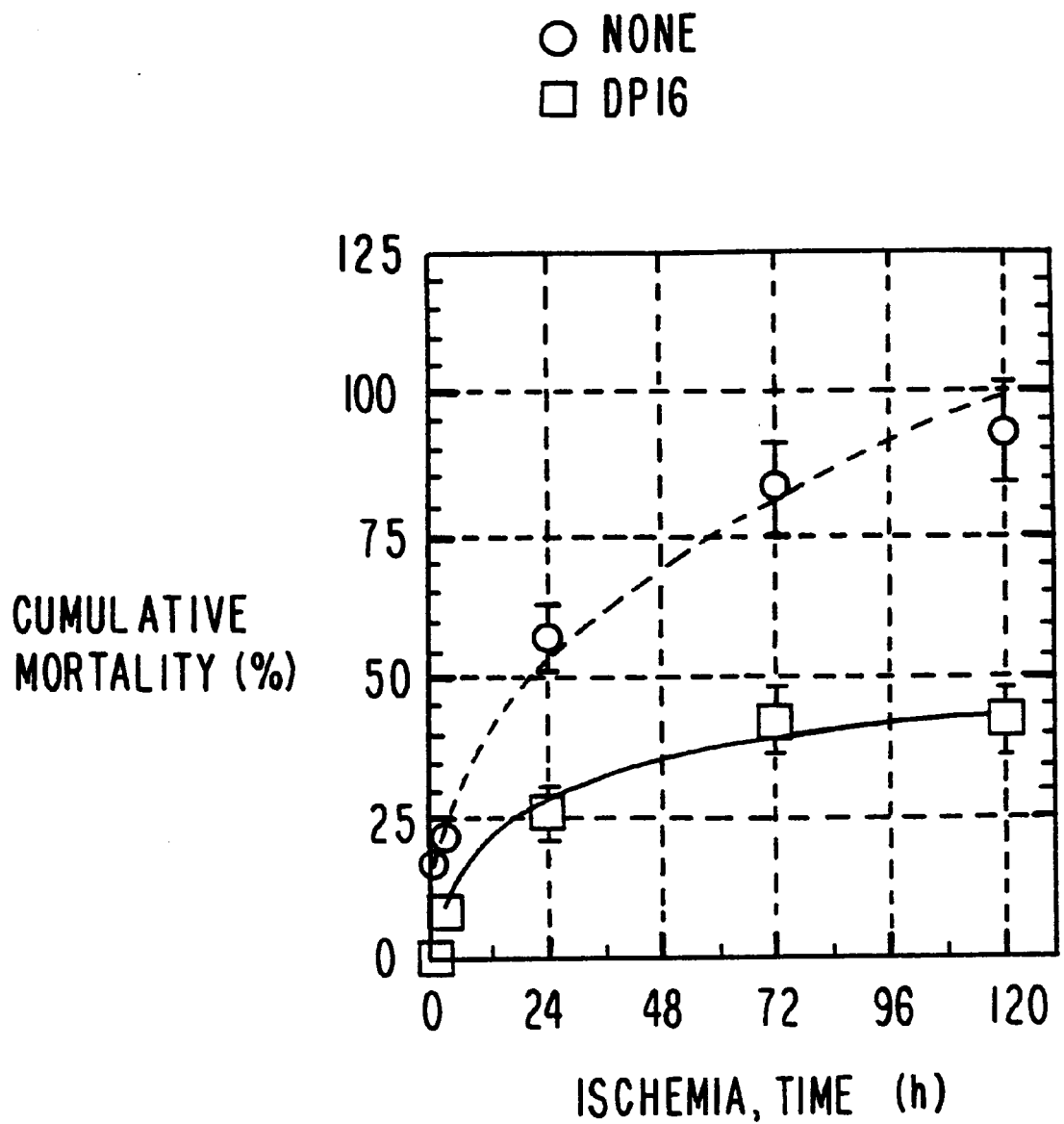

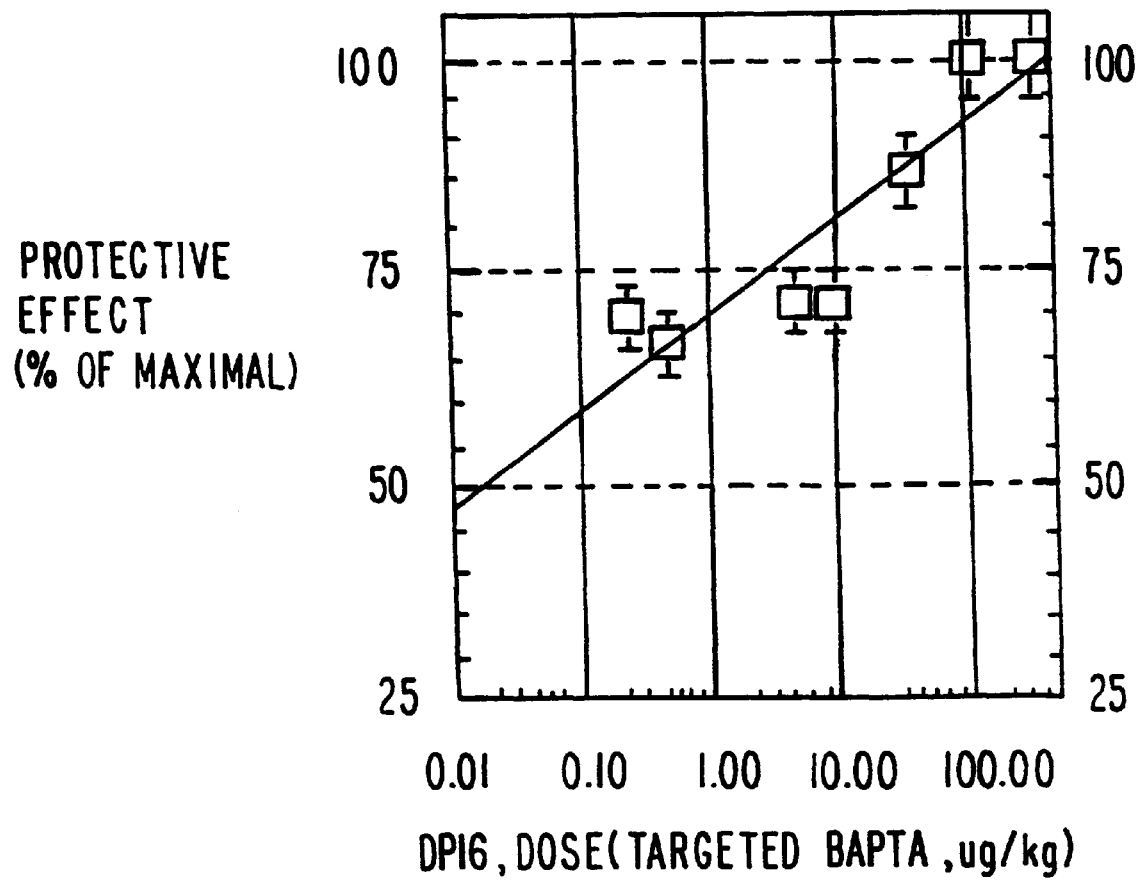

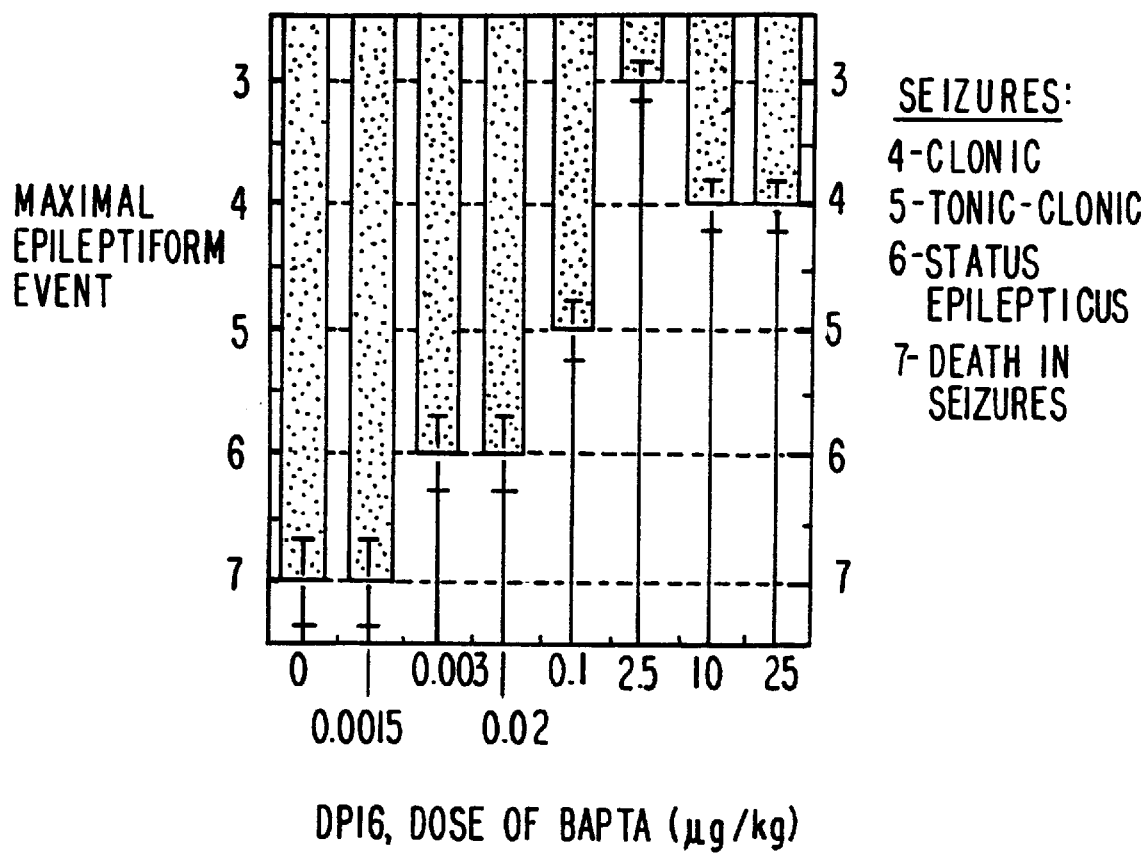

PRODRUG EFFECT ON METRAZOL INDUCED MINIMAL SEIZURES

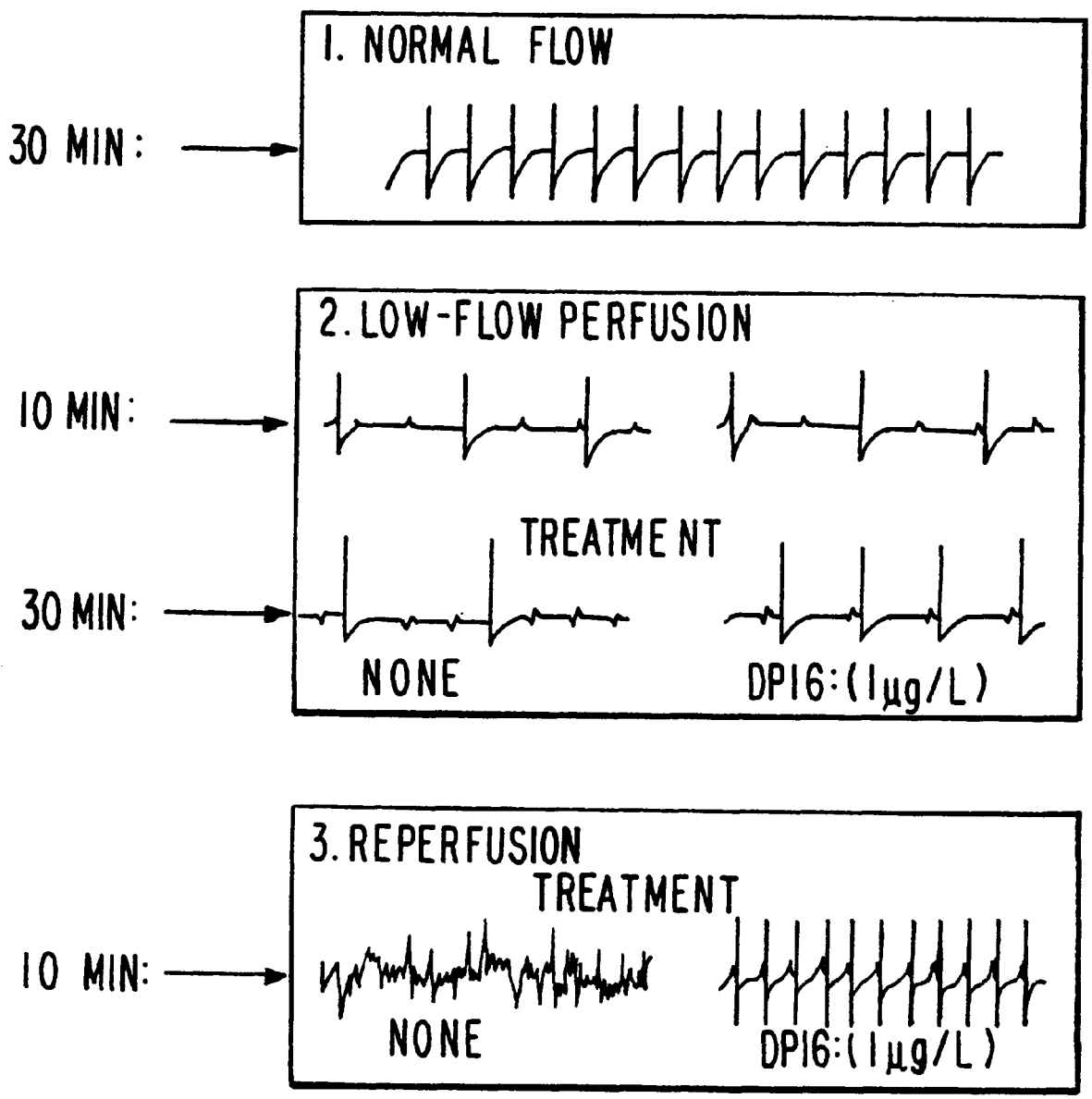

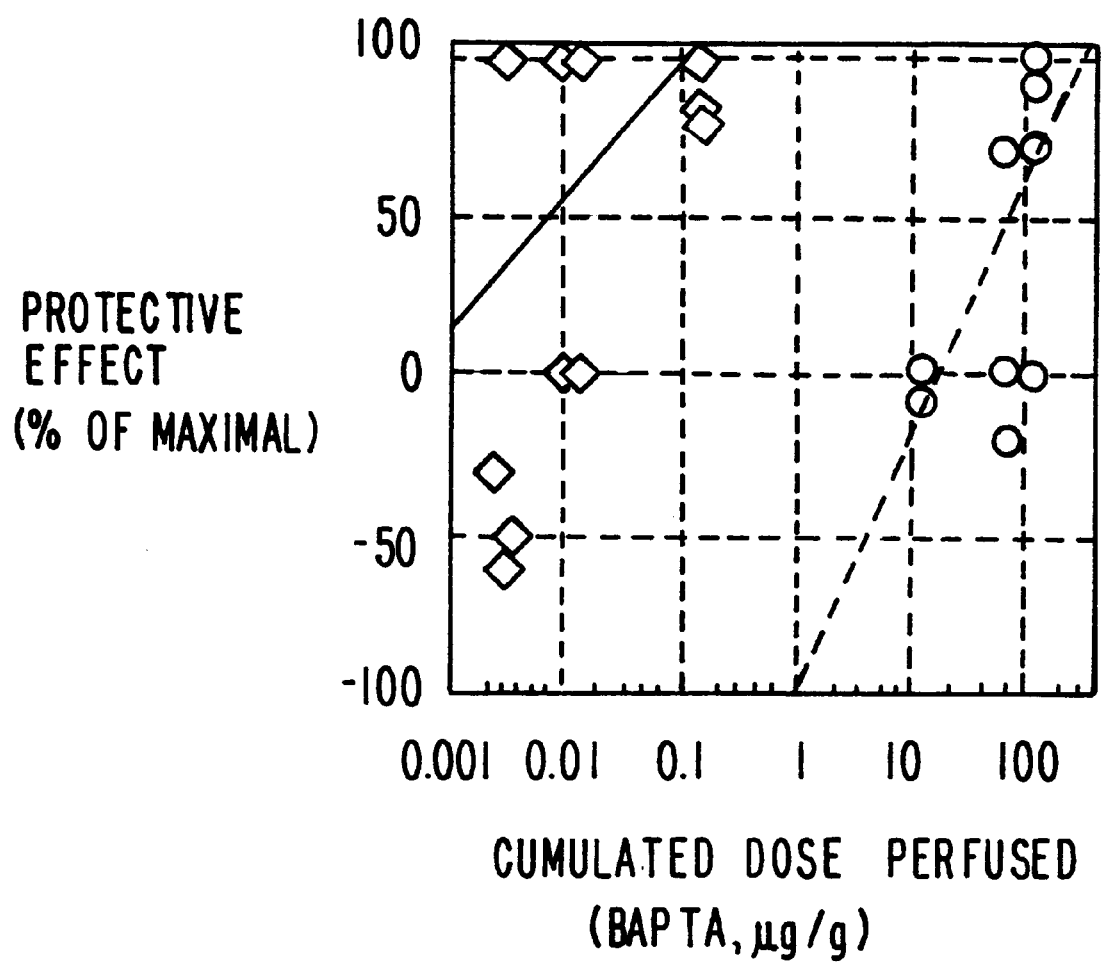

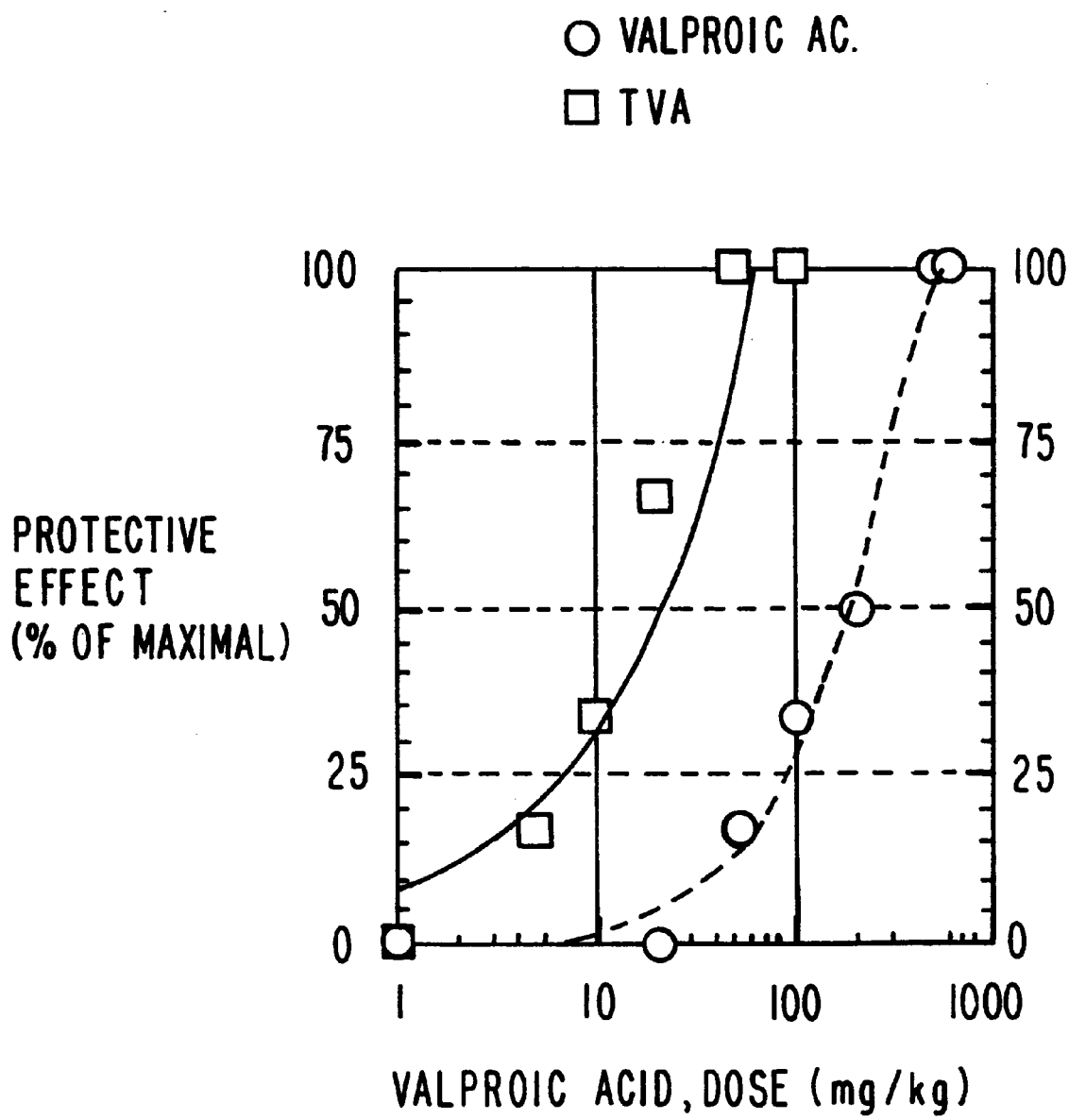

PRODRUGS WITH ENHANCED PENETRATION INTO CELLS

This application is a continuation of U.S. patent application Ser. No. 08/479,959, filed Jun. 7, 1995, which is a continuation-in-part of U.S. application Ser. No. 08/481,243, now U.S. Pat. No. 5,985,854, filed on Aug. 21, 1995 as a U.S. national stage application of PCT/GB94/00669, the disclosures of which are incorporated by reference herein in their entirety.

FIELD OF THE INVENTION

The present invention relates to a technique for treating a condition or disease in a mammal, including humans, related to supranormal intracellular enzyme activity, and to a prodrug useful in treating such a condition or disease.

BACKGROUND OF THE INVENTION

Many of the most prevalent diseases in humans including ischemia, stroke, epilepsy, asthma and allergy are all believed to be related to the phenomenon of cell hyperexcitation, a term used herein to denote supranormal intracellular enzyme activity. Certain pharmacological strategies are therefore aimed at inhibiting this detrimental degradative activity.

In contrast to such known strategies which are aimed at suppressing this degradative activity, it would be advantageous to be able to selectively target diseased cells characterized by enzyme hyperactivity, so as to introduce a pharmacologically active molecule in the form of a prodrug into the cell, whereby such hyperactivity would act on the prodrug, so that the pharmacologically active molecule accumulates in the diseased cells rather than in the healthy cells.

Different types of intracellular enzyme systems are known to be significantly elevated in pathological conditions, and may be used to achieve preferential release of the active drug compound within the diseased cells. Candidate enzymes that could be utilized to activate the prodrugs according to the present invention include lipases, proteases or glycosidases. By way of example, in many diseases cell membranes are broken down due to abnormal intracellular lipase activity.

The use of prodrugs to impart desired characteristics such as increased bioavailability or increased site-specificity on known drugs is a recognized concept in the state of the art of pharmaceutical development. The use of various lipids in the preparation of particular types of prodrugs is also known in the background art. In none of those instances are the prodrugs characterized in that they achieve preferential accumulation of the drug within the diseased cells of the organ, by activation with intracellular lipases. Rather, they provide for the drug to be transported to a specific site, or to be released within a specific organ.

This approach is exemplified in the case of the phospholipid prodrugs of salicylates and non-steroidal anti-inflammatory drugs disclosed in WO 91/16920 which, taken orally, protect the gastric mucosa and release the active principle in the gut.

In other examples of phospholipid prodrugs, formulation of the prodrugs into liposomes or other micellar structures is the feature that enables their preferential uptake, for instance by macrophages or by liver cells as in the case of the phospholipid conjugates of antiviral drugs disclosed in WO 90/00555 and WO 93/00910.

Generally, viral infection is not associated with supranormal phospholipase activity and antiviral phospholipid conjugates do not teach or suggest activation of the drug preferentially in the diseased cells, or in the infected cells as in the case of the phospholipid conjugates of antiviral nucleotides and anti-sense oligonucleotides, such as those disclosed in WO 90/00555, in WO 90/10448 and in NTIS Technical Notes, no. 9, page 630, Springfield, Va., US, 1984.

In other instances specific types of polar lipids are used to target the prodrugs to intracellular organelles as in the case of the antiviral and antineoplastic nucleosides disclosed in U.S. Pat. No. 5,149,794. Additional types of lipids have also been used in specific types of prodrugs such as EP A-325160 which discloses glycerin esters of ACE inhibitors, which form micelles absorbed from the intestine into the lymphatic system, thereby bypassing the liver and having increased access to the central nervous system, for use in the treatment of hypertension and cognitive dysfunction. The ACE inhibitors undergo enzymatic cleavage and exert their therapeutic effects extracellularly.

Other types of lipophilic carriers that facilitate intracellular transport are known in the art, as in CH A-679856 which discloses the use of salicyloyl-carnitine for the treatment of pain, and in WO 89/05358 which discloses modified oligonucleotide antisense drugs, transported into cells by attachment of apolar groups such as phenyl or naphthyl groups.

Different classes of pharmacologically active molecules can be administered as prodrugs according to the principles of the present invention. Candidates include anti-inflammatory drugs, anti-epileptic drugs, protease inhibitors, and anti-tumor drugs. A non-limiting example of such pharmacologically active molecules is a calcium chelating agent, which would have many advantages over drugs presently used for the treatment of calcium associated disorders.

Intracellular calcium is an important determinant for cell death, irrespective of the initial insult sustained by the cell. It may be involved in cell death in lymphocyte and killer cell mediated damage of target cells, in organ damage during transplantation, and in other types of tissue damage including ischemic insults. Calcium channel blockers or cell membrane permeable forms of calcium chelators have been suggested to protect against tissue injury or to decrease tissue damage. Thus, it will be apparent that the present invention has potential use (in the embodiment employing a calcium chelator) in relation to these circumstances The cell damage occurring in ischemia may be secondary to the influx and/or intracellular release of $Ca^{2+}$ ions (Choi, Trends Neurosci., 1988, 11, 465–469; Siesjo and Smith, Arzneimittelforschung, 1991, 41, 288–292). Similarly, calcium influx appears to play an important role in the genesis of epileptic seizures. Although a significant portion of intracellular calcium arrives from intracellular stores, current research suggests that calcium entry blockers may have anticonvulsant activity (see e.g. Meyer, 1989, Brain Res. Rev. 14, 227–243).

Drugs which are currently or potentially useful for treatment of calcium associated disorders include: (1) calcium channel blockers, (2) drugs affecting calcium balance by modification of intracellular calcium storage sites, and (3) intracellular calcium chelating agents. Calcium channel blockers used in clinical practice are represented by verapamil, Nifedipine and Diltiazem. The major toxicities associated with the use of such compounds involve excessive vasodilation, negative inotropy, depression of the-sinus nodal rate, and atrial ventricular (A-V) nodal conduction disturbances. Drugs affecting calcium mobilization and/or sequestration, like calcium channel blockers, exhibit rather narrow specificity.

Though the use of calcium chelators for reducing injury to mammalian cells is disclosed in WO 94/08573, there are no intracellular calcium chelating agents suitable for clinical requirements. Existing cell membrane permeable calcium chelators include acetoxymethyl esters such as EGTA-AM (ethylene-1,2-diol bis 2-aminoethyl ether N,N,N',N',tetra-acetic acid acetoxymethyl ester) EDTA-AM (ethylene-1,2-diamine tetra-acetic acid acetoxymethyl ester), and BAPTA-AM (1,2-bis 2-aminophenoxy ethan-N,N,N',N'-tetra-acetic acid acetoxymethyl ester). These known complex molecules, are digested by ubiquitous esterases, thus causing activation of the chelator in the intracellular space in a manner which is random and uncontrolled, being unrelated to cell activity.

It will also be self-evident that a similar concept can be applied to the treatment of conditions or diseases other than those related to the intracellular level of $Ca^{2+}$ ions. By way of example, if the active entity incorporated in the prodrug molecule is a protein kinase inhibitor, after administration of the prodrug the inhibitor would be accumulated in a cell exhibiting abnormal proliferation, thus providing potentially an important tool for use in antitumor therapy.

SUMMARY OF THE INVENTION

In accordance with one object of the invention, there are provided prodrugs which selectively undergo activation to release pharmacologically active compounds in hyperactivated cells. In accordance with another object of the invention, the pharmacologically active compound is released from the prodrug in response to enzyme activity in the targeted cells. In accordance with yet another object of the invention, the pharmacologically active compound, selectively accumulated in a cell characterized by a relatively raised level of enzyme activity therein, is trapped in the cell and therefore exhibits an enhanced desired activity therein.

The present invention accordingly provides in one aspect, a prodrug which is a covalent conjugate of a pharmacologically active compound and an intracellular transporting adjuvant, characterized by the presence of a covalent bond which is scission-sensitive to intracellular enzyme activity.

In another aspect, the present invention provides a technique for treating a condition or disease in a mammal, including a human, related to supranormal intracellular enzyme activity, which comprises administering to a mammal having such condition or disease, a pharmaceutically acceptable cell membrane permeable prodrug, the prodrug being a covalent conjugate of a pharmacologically active compound and an intracellular transporting adjuvant, characterized by the presence of a covalent bond which is scission-sensitive to intracellular enzyme activity, such that the bond is broken in response to such activity, whereby the pharmacologically active compound accumulates selectively within cells having supranormal intracellular enzyme activity, or in their immediate environment. In one particular aspect, the technique or method is used to treat, e.g., a human patient.

In yet another aspect, the invention provides pharmaceutical compounds for treating a condition or disease in a mammal related to supranormal intracellular enzyme activity, by selectively accumulating a pharmacologically active compound within cells having such activity, comprising a pharmaceutically acceptable cell membrane permeable prodrug, which is a covalent conjugate of the pharmacologically active compound and an intracellular transporting adjuvant, and is characterized by the presence of a covalent bond which is scission-sensitive to intracellular enzyme activity, such that the bond is broken in response to such activity. In one particular aspect, the pharmaceutical compounds are used to treat, e.g., a human patient.

BRIEF DESCRIPTION OF THE DRAWINGS

FIG. 2 compares cumulative mortality, with elapsed time (in hours), in a rat model of permanent cerebral ischemia in the presence (square) or absence (circle) of DP16.

FIG. 3 illustrates the dose-response curve for protection afforded by DP16 against generalized epileptic seizures induced by pilocarpine;

FIG. 4 illustrates the dose-response curve for protection afforded by DP16 against pilocarpine induced fatal epileptic events;

FIG. 6 illustrates results of experiments in hypoxia-reperfusion cardiopathology. The upper panel (1) shows an EKG of a heart during cardiac perfusion, the middle panel (2) shows an EKG of a heart during low flow perfusion, with and without 1 $\mu$g/L DP16 treatment and the lower panel (3) shows an EKG of a heart after reperfusion with and without 1 $\mu$g/L DP16 treatment.

FIG. 7 presents the superior protection of DP16 compared to BAPTA-AM in hypoxia-reperfusion induced cardiopathology;

FIG. 8 presents the dose response curve of TVA compared to valproic acid itself.

DETAILED DESCRIPTION OF THE INVENTION

Figure 1A:
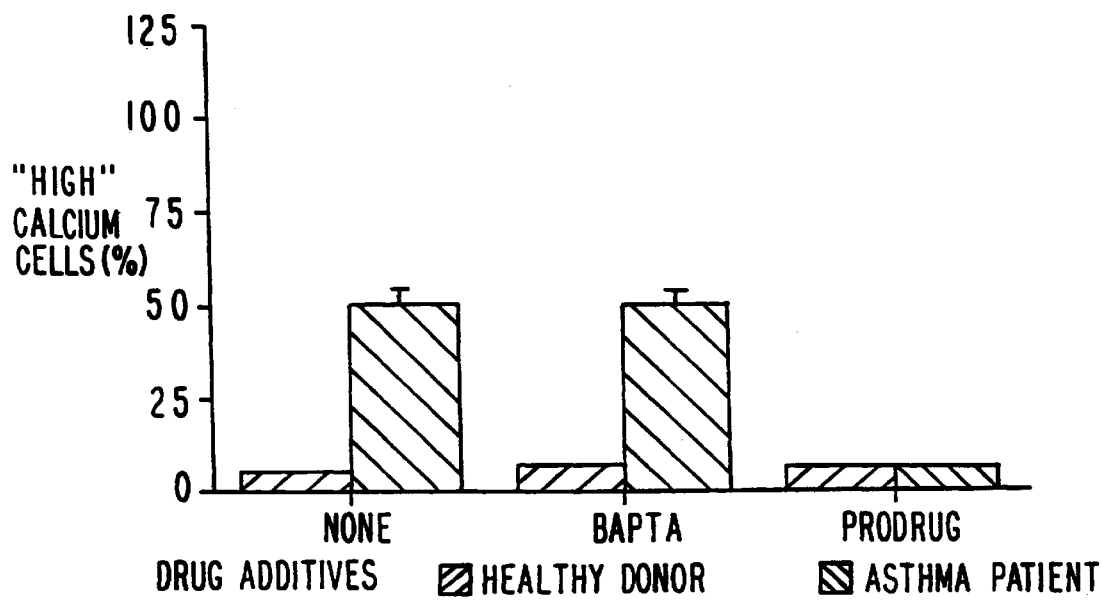
FIG. 1 presents the proportion of cells with elevated intracellular calcium levels in lymphocytes from a healthy individual and an asthmatic patient, and the effects of Prodrug 1 on these clacium levels, in comparison to treatment with BAPTA, before (Panel A) or after (Panel B) IgE stimulation.

Regulated Activation of Prodrugs by Hyperactive Intracellular Enzymes

According to the present invention, compounds are provided which are cell permeable prodrugs, comprising a pharmacologically active compound covalently bound to a lipophilic moiety which facilitates intracellular transport of the prodrug. As used herein and in the claims the term prodrug denotes a molecule which is incapable of exerting the pharmacological activity of the active compound. The active compound will exert its therapeutic effects after it is released from the prodrugs of the invention by the action of intracellular enzymes. The covalent bond of these prodrugs are scission sensitive to enzymes that are hyperactive in the cells that are affected, thereby providing selective activation of the pharmacological compound in the diseased cells.

In certain preferred embodiments, the pharmacologically active so molecule may be a cell impermeable drug. In these embodiments wherein the pharmacological compound is a cell impermeable drug, the compound will be selectively accumulated in the affected cells.

In other preferred embodiments, the pharmacological agents that are incorporated into the prodrugs of the invention, are themselves cell permeable molecules. In these embodiments the regulated activation of the active compound is achieved in those cells that require treatment, thereby significantly improving the therapeutic index of the pharmacological agent.

Different types of intracellular enzyme systems that are significantly elevated in pathological conditions may be used according to the present invention, to achieve the preferential release of the active drug compound within the diseased cells. Suitable enzymes that are to be utilized according to the present invention to activate the prodrugs include but are not limited to lipases, proteases or glycosidases. Members of these classes of enzymes are known to be elevated in a variety of diseases and disorders.

In currently preferred embodiments, the enzymes that activate the prodrugs are intracellular lipases. In most preferred embodiments the covalent bond of the prodrug is scission sensitive to phospholipases, a non limiting example of which are the phospholipases A2.

Distinction among the various phospholipases is based in part on their substrate specificity as well as their tissue localization, regulation and physicochemical attributes. The different specificities of these classes of phospholipases can serve as the basis of designing prodrugs which undergo specific activation, as suitable for the pathology to be treated.

The cleavage sites of the various phospholipases are herein depicted schematically in the following scheme.

Scheme 1

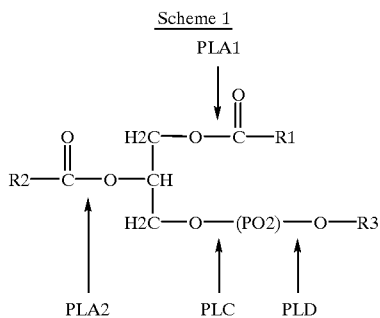

Prodrugs designed as substrates for phospholipase C (PLC) will much more useful for treatment of chronic excitatory disorders such as epilepsy. In this type of disorder PLC is involved in the earliest events of hyperactivation (preceding the physiological attack), while $PLA_2$ activation coincides with epileptic seizures.

Prodrug activation by PLC could be most preferred for targeting of antiepileptic drugs. Whereas prodrug activation by Phospholipase D (PLD) could by appropriate for targeting of antitumor drugs. In such prodrugs the P—O bond constituting the bond between the drug and the phospholipid would be scission-sensitive to enzyme PLD, thus releasing the antitumor agents intracellularly, and accumulating these inhibitors in cells having a supranormal level of PLD.

Phospholipases $A_2$ are a family of esterases that hydrolyze the sn-2 ester bonds in phosphoglyceride molecules releasing a free fatty acid and a lysophospholipid. Classification of the members of this family of enzymes is based on certain structural features and/or their localization in different cells and tissues. In principle, these enzymes are more active on aggregated phospholipid substrates compared with monomeric soluble substrates.

Phospholipid conjugates of drugs that will be cleaved by Phospholipases $A_2$ have previously been disclosed either a) to enhance penetration into cells; b) to enable formulation of drugs in liposomes; or c) as a form of "enterocoating" that prevents exposure of the gastric mucosa to the drug.

None of the previously disclosed uses of phospholipid-drug conjugates is an essential feature of the present methods of using these prodrugs, inasmuch as a) the present invention is effective even with drugs that are already capable of penetrating cells, as in the example of antiepileptic drugs; b) it is not desirable according to the current invention to formulate the prodrugs into liposomes since this achieves preferential distribution to specific organs (e.g., the liver) or to specific cell types(e.g., macrophages) rather than to diseased cells within an organ or cell population; c) the prodrugs according to the present invention are intended for parenteral administration in order to prevent their premature digestion by phospholipases in the digestive tract.

The prodrugs according to the present invention are contemplated to be useful in the treatment of patients in both human and veterinary medical practice. The prodrugs can be administered to a patient in need thereof by any of the conventional parenteral routes of administration, as may be appropriate for use in conjunction with the selective activation afforded by the prodrugs according to the invention for the disease or condition to be treated. These routes include, but are not limited to, intravenous (i.v.) injection, intramuscular (i.m.) injection, subcutaneous (s.c.) injection, infusion into a body cavity, cerebrospinal injection, localized infiltration into a target tissue, buccal absorption, and aerosol inhalation, in an amount effective to treat the disease or disorder. Formulations of the compounds of the present invention into pharmaceutical compositions suitable for the chosen route of administration may include any physiologically acceptable solutions, suspensions, emulsions, microemulsions, micellar dispersions, or the like, with any pharmaceutically acceptable excipients, as are known in the art. In addition, formulations may include various encapsulations or depots designed to achieve sustained release of the prodrug, as in those circumstances where a chronic disorder is to be treated.

According to one preferred embodiment of the present invention, protease inhibitors are provided which comprise a peptide or peptide analog which is a potent protease inhibitor, covalently bound to a phospholipid. These prodrugs are cell permeable molecules which are scission sensitive to abnormally hyperactivated phospholipases. Preferred protease inhibitors may inclue peptides, peptide analogs, or peptidomimetics.

A non-limiting example of such protease inhibitors are inhibitors of the neutral calcium-activated protease Calpain. Excessive activation of calpain may play a major role in a variety of disorders, including cerebral ischemia, muscular dystrophy and platelet aggregation (for review see Wang and Yuen, TIPS 15, 412–419, 1994). However, there are at present no selective and cell permeable calpain inhibitors. The improvement according to the present invention may be achieved with any of the known peptide or peptide analogs that are known calpain inhibitors, such as those reviewed by Wang and Yuen (ibid).

Within the scope of the present invention, additional embodiments are provided wherein the covalent bond of the prodrug, comprising said protease inhibitor, is scission sensitive to hyperactive intracellular proteases. Such further embodiments have a scission sensitive peptide bond between the protease inhibitor and a lipophilic carrier, thereby releasing the inhibitor in those cells that possess hyperactive protease activity. The use of lipophilic carriers to facilitate transport of peptide analogs across lipophilic barriers such as the blood brain barrier has been disclosed for instance in International patent application PCT/US93/09057. However, it is neither taught nor suggested in such disclosures that lipid conjugates may be utilized to achieve intracellular activation of a peptide drug.

In yet another embodiment, activation of the prodrugs is regulated by enzymes which are intracellular glycosidases, a non-limiting example of which is heparanase. Interaction of circulating cells of the immune system, as well as platelets, with the subendothelial extracellular matrix is associated with degradation of heparan sulfate by the specific endoglycosidase, heparanase. This enzyme is released from intracellular compartments in response to activation signals, implicating its involvement in inflammation and immunity. In contrast, various tumor cells express heparanase in a constitutive manner, in correlation with their metastatic potential. This enzyme is a suitable candidate for achieving regulated activation of antitumor drugs, or of drugs that modulate the immune response.

Prodrugs Activated by Phospholipases

The pharmacologically active compound may be by way of example a pharmacologically active carboxylic acid, when the adjuvant may comprise for example at least one pharmaceutically acceptable alcohol which is selected from glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lysoplasmalogens, lysophospholipids, lysophosphatidic acid amides, glycerophosphoric acids, lysophophatidalethanolamine, lyso-phosphatidylethanolamine and N-mono- and N,N-di-($C_{1-4}$)-alkyl and quaternary derivatives of the amines thereof.

Exemplary of pharmacologically active carboxylic acids are branched-chain aliphatic carboxylic acids (e.g. valproic acid), salicylic acids (e.g. acetylsalicylic acid), steroidal carboxylic acids (e.g. lysergic and isolysergic acids), mono-heterocyclic carboxylic acids (e.g. nicotinic acid) and poly-heterocyclic carboxylic acids (e.g. penicillins and cephalosporins). While pharmacologically active carboxylic acids are particularly described herein, as exemplary of the active compounds which may be conjugated with an intracellular transporting adjuvant, the invention is not limited thereto. Thus, by way of further example, it is entirely within the concept of the present invention to conjugate therapeutically active nucleic acid (including RNA and DNA) or fragments thereof with an intracellular transporting adjuvant.

In a preferred embodiment, the prodrug according to the invention comprises a conjugate of a calcium chelating agent and a lipid, and may thus be of potential use for treating diseases or conditions which are related to an unduly high level of intracellular $Ca^{2+}$ ions.

In a most preferred embodiment, the prodrug contains at least one covalent bond between the pharmacologically active compound and the intracellular transporting adjuvant, which covalent bond is scission-sensitive to intracellular enzyme activity, with the consequence that the greater part of the prodrug molecules will move freely in and out of normal cells without scission of such bond, whereas in the cells possessing the supranormal enzyme activity only, the scission-sensitive bond in a high proportion of prodrug molecules entering the cells will break. In those embodiments where the pharmacologically active compound is cell membrane impermeable the drug released from the prodrug will accumulate intracellularly, within the abnormal cells possessing supranormal enzyme activity.

Persons skilled in the art will appreciate in what manner the concept of the invention may be applied to conditions and diseases which are not necessarily related to an intracellular excess of calcium ions, so that in such other cases, the prodrug will incorporate an active compound which is not a calcium chelator but which will possess other desired pharmacological activity.

The prodrug which comprises a calcium chelating agent is, e.g., a partially or totally esterified carboxylic acid, which is an ester of:

(a) a pharmaceutically acceptable chelating agent for calcium having the formula (HOOC—$CH_2$—)$_2$—N—A—N—(—$CH_2COOH$)$_2$ where A is saturated or unsaturated, aliphatic, aromatic or heterocyclic linking radical containing, in a direct chain link between the two depicted nitrogen atoms, 2–8 carbon atoms in a continuous chain which may be interrupted by 2–4 oxygen atoms, provided that the chain members directly connected to the two depicted nitrogen atoms are not oxygen atoms, with (b) a $C_{3-32}$ pharmaceutically acceptable alcohol containing 1–3 OH radicals (e.g. such a $C_{3-6}$ alcohol, or e.g. a $C_{7-32}$ secondary monohydric alcohol);

and salts with alkali metals of the partially esterified carboxylic acids, as well as acid addition salts of such of the esterified carboxylic acids as contain one or more potentially salt-forming nitrogen atoms.

The choice of the preferred alcohol that is appropriate for any given prodrug is dependent on the intended therapeutic use of the conjugate. Thus alcohols below $C_{10}$ exhibit very low substrate specificity, whereas alcohols above $C_{12}$ or $C_{14}$ are very good substrates for the phospholipases and will therefore be readily activated. Regulated activation will best be achieved by the intermediate length alcohols such as $C_2$–$C_{10}$, and these will be preferred for the treatment of persistent or chronic disease states or disorders.

In contradistinction, in certain disease states that require the rapid release of the active agent the most preferred alcohols will be the longer chain alcohols, This is most suitable for conditions involving acute onset pathology such as in the treatment of epilepsy with the prodrugs of the invention. Further, in the case where there are relatively minimal differences in intracellular enzymatic activity between normal and diseased or disordered cells, relatively shorter chain alcohols may be selected.

The ester of choice may be one in which the linking radical A is a member selected from the group consisting of —($CH_2CH_2$)$_m$— where m=1–4, in which 2–4 of the carbon atoms not attached to nitrogen may be replaced by oxygen atoms, and —CR═CR—O—$CH_2CH_2$—O—CR'═CR'—, where each of the pairs of radicals R—R and R'—R', together with the attached —C═C— moiety, complete an aromatic or heterocyclic ring containing 5 or 6 ring atoms, the ring completed by R—R being the same as or different from the ring completed by R'—R'.

In particular embodiments, the linking radical A may be, e.g., selected from —$CH_2CH_2$— and —$CH_2CH_2$—O—$CH_2CH_2$—O—$CH_2CH_2$—; or it may be e.g. —CR═CR—O—$CH_2CH_2$—O—CR'═CR'—, where each of the pairs of radicals R—R and R'—R', together with the attached —C═C— moiety, complete an aromatic or heterocyclic ring which is selected from the group consisting of furan, thiophene, pyrrole, pyrazole, imidazole, 1,2,3-triazole, oxazole, isoxazole, 1,2,3-oxadiazole, 1,2,5-oxadiazole, thiazole, isothiazole, 1,2,3-thiadiazole, 1,2,5-thiadiazole, benzene, pyridine, pyridazine, pyrimidine, pyrazine, 1,2,3-triazine, 1,2,4-triazine, and 1,2-, 1,3- and 1,4-oxazines and thiazines, the ring completed by R—R being the same as or different from the ring completed by R'—R'. In a particularly preferred embodiment, the linking radical A is —CR═CR—O—CH$_2$CH$_2$—O—CR'═CR'—, where each of the pairs of radicals R—R and R'—R', together with the attached —C═C— moiety, completes the same or different rings selected from unsubstituted and substituted benzene rings, in which substituted benzene rings contain 1–4 substituents selected from the group consisting of $C_{1-3}$-alkyl, $C_{1-3}$-alkoxy, F, Cl, Br, I and CF$_3$, or a single divalent substituent which is —O—(CH$_2$)$_n$—O— and n=1–3.

It is presently preferred that the calcium chelating agent incorporated in the prodrug is selected from ethylene-1,2-diamine-N,N,N',N'-tetra-acetic acid, ethylene-1,2-diol-bis-(2-aminoethyl ether)-N,N,N',N'-tetraacetic acid and 1,2-bis-(2-aminophenoxy)ethane-N,N,N',N'-tetraacetic acid.

As mentioned above, $C_{3-32}$, e.g. $C_{3-6}$, alcohol referred to above contains 1–3 OH radicals. When 2 OH radicals are present, one of them may be esterified or otherwise derivatized, and when 3 OH radicals are present, either 1 or 2 of the OH radicals may be esterified or otherwise derivatized. Any carbon atoms in the esterifying or otherwise derivatizing group(s) are not counted for the purpose of the e.g. 3 to 6 carbon atoms which may be contained in the pharmaceutically acceptable alcohols.

Thus, these alcohols may comprise, e.g., at least one member of the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lysoplasmalogens, lysophospholipids, lysophosphatidic acid amides, glycerophosphoric acids, lysophdphatidalethanolamine, lysophosphatidylethanolamine and the N-mono-$C_{1-4}$-alkyl, N,N-di-$C_{1-4}$-alkyl and quaternary ammonium derivatives of such of the foregoing as are amines. An example of a $C_{7-32}$ secondary alcohol is 1-myristylmyristyl alcohol.

The person skilled in the art will appreciate that the prodrug of the present invention can be tailored in such a manner that the desired pharmacologically active entity is released by action of the specific enzyme known to be the source of enzyme hyperactivity in the condition or disease being treated. For example, membrane-associated calcium-independent plasmalogen-selective PLA$_2$ activity has been found to increase over 400% during two minutes of global ischemia (P<0.01), was greater than 10-fold (near to the maximum) after only five minutes of ischemia, and remained activated throughout the entire ischemic interval examined (up to 60 minutes), see Ford et al, J. Clin. Invest., 1991, 88(1): 331–5. These facts suggest attaching the pharmacological active entity to the 2-position in a glycerophosphoric acid derivative, and that use of a lysoplasmalogen may possibly be more effective as the intracellular transporting adjuvant, to which the active entity is attached covalently, than a lysophospholipid.

Many events (e.g. cytotoxic chemicals, physical stimuli and infective agents) causing damage of the cell membrane can trigger a cascade leading ultimately to a condition which mimics ischemic damage(Robbins et al, Pathological Basis for Disease, 1984, p. 10, W. B. Sanders Co.). The present invention will potentially be of use for protecting cells in these circumstances, by introduction of a calcium chelator intracellularly.

In this connection, it is noted that the antitumor drug Adriamycin, which has been reported to inhibit Na—Ca exchange and to overload the sarcoplasm with calcium, could induce contractile heart failure; this would be consistent with the hypothesis that calcium overload, in absence of ischemia, can leave behind long-lasting contractile dysfunction (Kusuoka et al, J. Cardiovasc. Pharmacol., 1991, 18(3): 437–44).

As indicated above, the concept of the present invention is not restricted to the treatment of conditions or diseases related to the intracellular level of Ca$^{2+}$ ions, so that the materials used in practicing the invention are not restricted to calcium chelators. Thus for example, the pharmacologically active compound may be e.g. an antiepileptic compound such as valproic acid.

In this connection, it is contemplated that application of the present invention in this embodiment would enable a much lower effective dose of valproic acid to be used than is otherwise the case, thus potentially substantially reducing the occurrence of undesired side-effects. In principle, any of the range of alcohols, and examples thereof, mentioned above in connection with esterification of calcium chelators may also be applied to the esterification of valproic acid in accordance with the concept of the present invention.

In a non-limiting embodiment, valproic acid may be esterified with, e.g., 1-heptanoyl-sn-glycero-3-phosphorylcholine.

In another particular embodiment, the pharmacologically active compound incorporated in the prodrug of the invention is a protein kinase inhibitor. Where the protein kinase inhibitor is a carboxylic acid, the prodrug may be e.g. an ester thereof with a pharmaceutically acceptable alcohol such as glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lysoplasmalogens, lysophospholipids, lyso-phosphatidic acid amides, glycerophosphoric acids, lysophophatidalethanolamine, lyso-phosphatidylethanolamine and N-mono- and N,N-di-($C_{1-4}$)-alkyl and quaternary derivatives of the amines thereof. Such a carboxylic acid is e.g. protein kinase inhibitor K252b from Nocardiopsis sp.

Where the protein kinase inhibitor contains an amine group with a replaceable N-linked hydrogen atom, the prodrug may be e.g. an amide thereof with a phosphoric acid derivative selected from glycerophosphoric acids, O-acylated or etherified glycerophosphoric acids, and monoacylated monoetherified glycerophosphoric acids. Such protein inhibitors are e.g. isoquinoline-5-sulfonamide N-substituted by an acyclic or heterocyclic aminoalkyl radical such as NHCH$_2$CH$_2$NHCH$_3$ and 2-methylpiperazin-1-yl. Where the protein kinase inhibitor contains at least one phenolic hydroxy group, the prodrug may be e.g. an ester thereof with a phosphoric acid derivative selected from glycerophosphoric acids, O-acylated glycerophosphoric acids, etherified glycerophosphoric acids, and monoacylated monoetherified glycerophosphoric acids. Such a protein kinase inhibitor is e.g. 4',5,7-trihydioxyisoflavone.

In another particular embodiment, the pharmacologically active compound incorporated in the prodrug of the invention is an antitumor agent. The ordinary artisan will understand that the principle of the invention can be applied to any suitable antitumor agent by linking such an agent to an intracellular transporting adjuvant as described above, to which the pharmacologically active compound is attached covalently. The linkage is selected so that supranormal intracellular enzyme activity characteristic of target cells (e.g., tumor cells) will cleave the intracellular transporting adjuvant from the pharmaceutically active compound. In a particular aspect,the antitumor agent is, for example, a folic acid agonist such as a 4-amino analog of folic acid. A representative member of this class of compounds is methotrexate. Methotrexate and related compounds are known to the art as effective antitumor agents that have also been used in the treatment of psoriasis and in the modulation of cell mediated immunity. Impaired transport of methotrexate into target cells is believed to be one mechanism for the development of tumor resistance to that drug (Goodman and Gilman's, THE PHARMACOLOGICAL BASIS OF THERAPEUTICS, 8Th Ed., 1990, Pergamon Press, hereby incorporated by reference in its entirety). Thus, methotrexate linked to a cell membrane permeable adjuvant-cleavable by supranormal intracellular enzyme associated with a diseased or disordered target cell will enhance the specificity and effectiveness of such treatment of tumor cells by antitumor drugs, such as, e.g, methotrexate or other folic acid antagonists. Prodrug derivatives of methotrexate are also contemplated to be used to treat any of the other aforementioned conditions treatable by methotrexate When selecting the intracellular transporting adjuvant for the purposes of the present invention, the skilled person will of course take into consideration the necessity for avoiding such adjuvants, e.g. certain 1,2-diacylglycerols, which are activators of protein kinase C (see Lapetina et al, J. Biol. Chem., 1985, 260: 1358 and Boynton et al, Biochem. Biophys. Res. Comm., 1983, 115: 383), or intracellular transporting adjuvant which are likely to give rise to undesirable products such as these in the cell. In addition, the artisan will appreciate that the selected linker to the intracellular transporting adjuvant should be selected to avoid interaction with desired pharmacological activity and to avoid rapid, nonspecific intracellular degradation after specific cleavage.

The following examples are to be construed in a non-limiting fashion and represent certain preferred embodiments of the invention. One skilled in the art can readily devise many variations and modifications of the principles disclosed herein without departing from the scope of the invention.

DESCRIPTION OF THE PREFERRED EMBODIMENTS

The following examples illustrate various aspects of the present invention and are not to be construed to limit the claims in any manner whatsoever

EXAMPLES

Example 1

Preparation of Esters of Heptanoyl-sn-3-glycerophosporylcholine (Prodrug-1 and Prodrug-2).

Introduction

"Prodrug-1" is the name used herein to denote a 1:1 ester of 1,2-bis-(2-aminophenoxy)ethane-N,N,N',N'-tetraacetic acid (BAPTA) with the choline derivative $ROCH_2$—CH(OH)—$CH_2O$—($PO_2$)—$OCH_2N^+(CH_3)_2$, wherein R is heptanoyl. BAPTA is a calcium chelator, to which the human cell membrane is normally impermeable, whereas the cell membrane is permeable to prodrug-1, which is not a calcium chelator per se. The carboxylic ester links in prodrug-l are digestible by $PLA_2$, so that activated cells such as IgE lymphocytes should exhibit a selective intracellular accumulation of BAPTA, compared to the unactivated cells, with the result that the $[Ca^{2+}]_i$ level in the activated cells should be reduced when compared with unactivated cells. "Prodrug-2" is the 1:2 ester of BAPTA with the depicted choline derivative.

Procedure (a) Diheptanoyl-L-α-lecithin

In a dry 3-neck 500 ml flask equipped with oil-sealed stirrer, $CaCl_2$ tube and dropping funnel, were placed 100 ml of 5 mm diameter glass beads and 11.0 g (0.01 mole) of $CdCl_2$ adduct of synthetic L-α-glycero-phosphorylcholine. The flask was immersed in an ice-water bath, and to the rapidly-stirred mixture there was added a thin stream of 29.7 g (0.2 mole) freshly prepared heptanoyl chloride dissolved in 60 ml chloroform, followed by 11 ml (0.14 mole) anhydrous pyridine dissolved in 100 ml chloroform(anhydrous, alcohol-free). After 30 minutes, the bath temperature was raised to 25° C. and stirring continued for 2 hours. The reaction mixture was poured through a filter-less Buchner, the glass beads washed with 3×50 ml chloroform and the combined filtrates clarified by centrifugation. The supernatant was concentrated under reduced pressure, the residue kept for several hours at 0.1 mmHg vacuum and bath temperature 30–35° C. to remove most excess pyridine, and was then stirred with 500 ml anhydrous acetone for 10 minutes, and centrifuged. The precipitate was treated similarly with 2×100 ml anhydrous acetone and 2×100 ml anhydrous ether.

The residual solid material was dried under reduced pressure and freed of the last traces of cadmium chloride and pyridine hydrochloride, by dissolving in 200 ml of a 5:4:1 by volume mixture of chloroform/methanol/water, and passing the solution through a 120 cm long×2.5 cm diameter column containing an equivolume mixture of Amberlites IR-45 and IRC-50. The column was washed with 500 ml of the same chloroform/methanol/water mixture, the combined effluents were concentrated to dryness under reduced pressure from a bath at 40–45° C., and the residue dried at 0.1 mm vacuum and 45° C. The crude product was purified by precipitation from a solution in 50 ml chloroform, with 150 ml acetone, centrifugation and recrystallization of the precipitate, 2.3 g (47.6%) from chloroform and ether. (Di-octanoyl-L-α-lecithin can be prepared similarly.)

(b) 1-Heptanoyl-sn-3-glycerophosphorylcholine.

A solution of the product of part (a) (1.2 mmol) in a mixture of ether (196 ml) and methanol (12 ml) was stirred vigorously in presence of $(HOCH_2)_3C$—$NH_2.HCl$ (50 ml of 0.1M, pH 8.7) containing $CaCl_2$ (0.72 mM) and 5 mg of crude rattle snake venom (*Crotalus adamanteus*) as a source of phospholipase $A_2$, at 37° C. for 3 hours. The reaction was monitored by TLC (70:25:4 by volume chloroform/methanol/water). After completion of reaction, the organic layer was separated, and the aqueous layer was washed with ether and then lyophilized. The residue was extracted with 2:1 by volume chloroform/methanol and centrifuged. On evaporation of the clear supernatant, the title product was obtained in 90% yield. Thin layer chromatography using 70:25:4 by volume chloroform/methanol/water showed that it was free from starting material and heptanoic acid. Any fatty acid in the product can however be remove by crystallization from ethanolether.

Note: this is a general method for scission of the glycerol-2-ester bond. (Octanoyl-sn-3-glycerophosphoryl-choline can be prepared similarly.)

(c) Prodrug-1 and Prodrug-2

A solution of the product of part (b) (0.5 g, 1.04 mmol) in chloroform (15 ml, freshly distilled over $P_2O_5$) was added to a solution of BAPTA (0.495 g, 1.03 mmol for the monoester Prodrug-1, or 0.248 g, 0.51 mmol for the diester Prodrug-2), N,N'-dicyclohexyl-carbodiimide (0.214 g, 1.03 mmol) and 4-dimethylaminopyridine (0.025 g, 0.202 mmol) and $HCONMe_2$ (20 ml, freshly distilled over $CaH_2$) under a nitrogen atmosphere, and the mixture was stirred at room temperature for two days. The reaction was monitored by TLC (65:35:5 by volume chloroform/methanol/water).

The precipitate was removed by filtration, the filtrate was concentrated by evaporation in vacuo at 35° C. and the residue was dissolved in 2:1:2 by volume chloroform/isopropanol/water). The organic layer was separated, dried ($Na_2SO_4$) and then passed through a 20 cm long×1.8 cm diameter column of silicic acid (Bio-Sil-HA). The column was thoroughly washed with chloroform until free from BAPTA (TLC) and then eluted with a gradient of chloroform/methanol (1:1 by volume) to pure methanol, the elution being monitored by TLC. The eluted fractions were combined and concentrated by evaporation. The desired title product (i.e. Prodrug-1 or Prodrug-2, depending on the number of molar equivalents of BAPTA used) was crystallized from ether and dried in vacuo over $P_2O_5$ at 30° C.: yield 0.3 g (30%).

It will be apparent that the corresponding triester or tetraester may be obtained by varying appropriately number of molar equivalents of BAPTA. (The analogous octanoyl esters are prepared similarly.)

Example 2

Application of Prodrug-1 for Reduction of the Intracellular Calcium Level in Hyperactivated Cells.

Method

Intracellular free $[Ca^{2+}]_i$ content was monitored by flow cytometry using the $Ca^{2+}$-sensitive dye fluo-3/AM (Molecular Probe Inc., OR)(Minta, Kao and Tsien, 1989, J. Biol. Chem. 264:8171–8178). Cells obtained from donor blood and those from the blood of an asthmatic patient were further washed twice in DMEM and resuspended to a concentration of $10^7$ cells/ml. Fluo-3/AM (1 mM) was prepared in DMSO augmented with the nonionic surfactant Pluronic F-127 (Wyandotte Corp., MI). Aliquots of fluo-3/AM stock solution were added to cell suspensions in DMEM/HEPES at a final concentration of 3 μM (loading buffer). Loading was allowed to proceed for 30 min. at 37° C. and continued for 1 hour at 23° C. with gentle agitation. Cells were then adjusted to desired concentrations using fresh DMEM/HEPES, supplemented with 2% horse serum. Autofluorescence was eliminated by setting the threshold sensitivity above the levels obtained in absence of dye. Fluorescence intensity data was collected from 5000 single cells and values were expressed as arbitrary fluorescence units. Prodrug-1 (1 mM) was prepared in DMSO and added when appropriate at a final concentration of 3 μM to the cells for 5 min. prior to calcium treatment.

Results

Figure 1B:
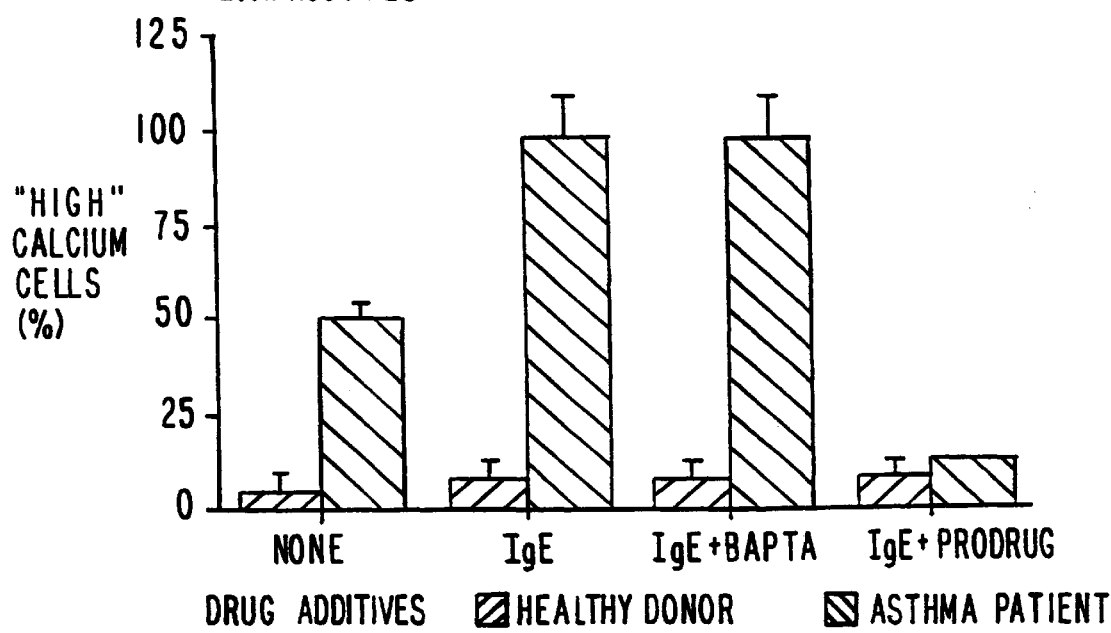

Lymphocytes from donor blood and from the blood of an asthmatic patient were exposed to prodrug-1. Accumulation of the liberated BAPTA chelator within the cell was estimated by measurement of $[Ca^{2+}]_i$, by flow cytometry using fluo-3/AM as described above. The results are presented in FIG. 1; in which the $[Ca^{2+}]_i$ levels are shown as follows:

Panel A presents a comparison between the lymphocytes isolated from a healthy domor and those of the asthmatic patient, in terms of the proportion of cells having high intracellular free calcium.

Panel B presents a comparison of the same cell populations after stimulation with IgE. As shown in panel B, the prodrug also provides protection against high intracellular calcium in IgE stimulated cells.

It was found that lymphocytes from an asthmatic patient have a dual partition according to the $[Ca^{2+}]_i$ level. About 50% of the cells exhibit a high $[Ca^{2+}]_i$ level indicating cell hyperactivation (panel A), while the second part of the population is similar to the normal one. In the case where the cells have been treated with prodrug-1, the population of hyperactivated cells is back to normal, while the population of non-activated cells remains unchanged. These data demonstrate that prodrug-1 provides selective accumulation of the chelator within activated, but not in non-activated cells. BAPTA itself, which is a cell impermeable molecule is ineffective in reducing the intracellular calcium levels, in either stimulated or untreated cells.

Example 3

Prodrugs of Potential Application in the Treating Tumors

Introduction

In this Example, there are presented a number of illustrative embodiments of the present invention in which a prodrug comprises a protein kinase inhibitor. After administration of the prodrug, the inhibitor would be accumulated in a cell exhibiting abnormal proliferation, thus providing potentially an important tool for use in antitumor therapy.

(i) The compound $QSO_2\tilde{N}^{\wedge}$ where Q=5-isoquinolyl and $\tilde{N}\tilde{N}^{\wedge}=NHCH_2CH_2NHCH_3$, is a selective inhibitor of cAMP-dependent protein kinase: Hidaka et al, Biochemistry, 1984, 23: 5036, and Tash et al, J. Cell Biol., 1986, 103: 649. Similarly, the compound $QSO_2\tilde{N}$ where Q=5-isoquinolyl and $\tilde{N}$=2-methylpiperazin-1-yl, is a potent inhibitor of cyclic nucleotide dependent protein kinase and protein kinase C: Hidaka et al, loc cit, and Kikuchi et al, Nucl. Acid Res., 1988, 16: 10171. These compounds can be covalently conjugated to an intracellular transporting adjuvant by methods known to persons of the art, e.g. illustratively:

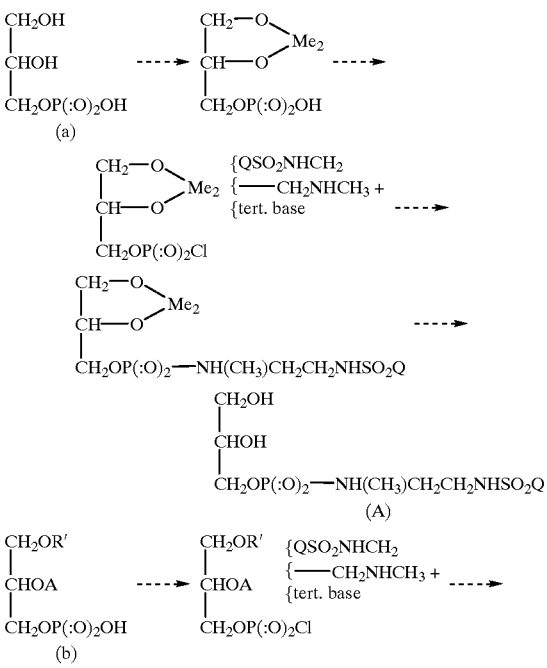

-continued

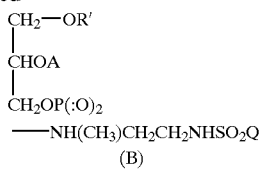

In scheme (b), R is an aliphatic hydrocarbon group such as is found in plasmalogens (or it may be inserted in a conventional synthetic procedure) and A is an aliphatic acyl radical, e.g. lauroyl, myristoyl, palmitoyl, stearyl and oleyl.

The compound QSO$_2$NN^ where Q=5-isoquinolyl and NN^=2-methylpiperazin-1-yl, may be attached in a similar manner by means of the piperazine N$^4$ atom.

It would be expected that the P—N bond in prodrugs (A) and (B) depicted above would be scission-sensitive to enzyme PLD, thus releasing the described protein kinase inhibitors intracellularly, and accumulating these inhibitors in cells having a supranormal level of PLD.

(ii) 4',5,7-trihydroxyflavone is an inhibitor of tyrosine specific protein kinase: Akiyama et al, J. Biol. Chem., 1987, 262: 5592. This compound can be conjugated to an intracellular transporting adjuvant by methods,(a) and (b) described in part (i), above. The illustrative conjugates would have structures (C) & (D):

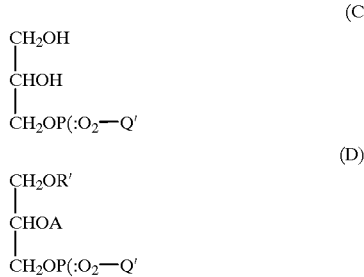

where R' and A have the meanings given above and Q' is the residue of 4',5,7-trihydroxyisoflavone from which one phenolic hydrogen atom has been removed and which is thus attached to the rest of the molecule by an O atom forming a P—O bond. It would be expected that this P—O bond in prodrugs (C) and (D) depicted above would be scission-sensitive to enzyme PLD, thus releasing the described protein kinase inhibitors intracellularly, and accumulating these inhibitors in cells having a supranormal level of PLD.

(iii) Protein kinase inhibitor K252b from Nocardiopsis sp. is a carboxylic acid believed to have the following formula:

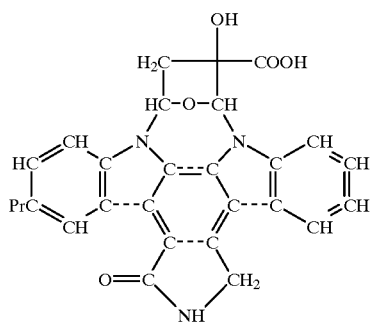

This compound can be conjugated to an intracellular transporting adjuvant, e.g., by the method described in Example 1, above. Exemplary conjugates are esters of the carboxylic function in the above formula, with e.g. heptanoyl-sn-3-glycerophosphoryl-choline or octanoyl-sn-3-glycerophosphoryl-choline.

Example 4

Preparation and Biological Properties of DP16.

4.1) Preparation of DP16

"DP16" denotes herein to denote a 1:1 ester of BAPTA with the phosphorylcholine derivative ROCH$_2$—CH(OH)—CH$_2$O—(PO$_2$)—OCH$_2$N$^+$(CH$_3$)$_2$, where R is hexadecanoyl. DP16 was prepared according to the method described in Example 1.

4.2) DP16 Testing in Models of Brain Ischemia a) Permanent Ischemia Model in Rats:

Bilateral ligation of the common carotid arteries is the simplest and most direct approach for inducing permanent partial ischemia. In the rats there is almost 64% mortality 24 h later. The causes of mortality are largely brain swelling (edema) and focal lesions (infarcts). Permanent partial global is achieved by isolation of the common carotid artery through an incision on the ventral surface of the neck. The salivary glands are moved laterally and the carotid sheath exposed. Both the vagus and sympathetic nerves are separated from the common carotid artery, which is then permanently ligated. Sprague-Dawley rats (250–300 g) were anesthetized with halothane or by intramuscular injection of 0.1 ml Ketamine (0.1 g/ml, Parke Davis UK) and 0.1 ml Rompun (2%, Bayer, FRG) per 300 g body weight. DP16 was administered intraperitoneally (i.p., 0.001–0.1 mg/kg) when appropriate following the artery ligation. Every experimental and control group included 14 male rats. Statistical analysis was performed according to t-test criteria.

b) Embolic Stroke:

Sprague-Dawley rats (300 g) are anesthetized with halothane. The right common carotid artery is exposed and the external carotid and pterygopalatine arteries are ligated with No. 0 silk thread. The common carotid artery is cannulated with a plastic tube previously filled with heparinized saline. The cannula is then injected (0.5 ml gas-tight Hamilton syringe) with a suspension of polystyrene spheres, followed by a flush of 0.5 ml saline. The common carotid artery is then permanently ligated. The polystyrene 15 μm spheres are prepared in 0.05% Tween-80 in normal saline followed by 5 min. of full power sonication. A 100 μl aliquot is taken and immediately transferred to the syringe.

c) Ischemic Fetal Brain Model:

Sprague-Dawley pregnant rats were used at 20 days gestation. Animals were anesthetized by intramuscular injection of 0.1 ml Ketamine (0.1 g/ml, Parke Davis, UK) and 0.1 ml Rompun (2%, Bayer, FRG) per 300 g body weight. An abdominal incision was performed and the two uterine horns were exposed and kept moist throughout the surgery. Intracerebral injection of 1–2 mCi/2 ml [$^3$H] arachidonic acid (Na+, 240 mCi/mmol from New England Nuclear, Boston, Mass.) and/or 1.5 mCi/2 ml [$^{14}$C]palmitic acid (Na+, 819 mCi/mmol from Amersham, Searle, UK) in isotonic salt solution containing NaHCO$_3$ (1.32 g %), into the embryos was performed through the uterine wall into the fontanellae. Custom made syringes (33 gauge, 0.375" length from Hamilton, Reno, Nev.) were used to reduce brain edema. After injection fetuses were returned to the abdominal cavity for maintenance at physiological temperature. After 1 h they were subjected to blood flow restriction for 20 min. (restriction session) by clamping the blood vessels in the placenta manifold. Whenever desired, circulation was restored for 30 min. by removal of the clamps (reperfusion session). At all times both restricted and sham-operated fetuses were maintained in the abdominal cavity before surgical delivery. After delivery through a transverse cut in the uterus, viable fetuses with no apparent edema were killed without delay and excised fetal brains were immediately homogenized in suitable organic solvents for further treatment.

d) Fetal Cerebral Hemispheres Model:

Rat fetuses were removed from the uterine horns in a viable state and their cerebral hemispheres were dissected within 15 sec after decapitation. The cerebral hemispheres freed of blood and meninges were separated and each (50±2.5 mg) was placed in a well of a 24-well Falcon culture dish. Tissue was quickly washed twice in cold Dulbecco's Modified Eagle Medium (DMEM, Grand Island Biol. Co) and then incubated at 37° C. in 0.6–1.2 ml DMEM flushed with oxygen and supplemented with various additives. Aliquots of incubation medium (0.1 ml) were taken for eicosanoid determination by a radioimmunoasay (RIA) technique. After acidification with 5 ml formic acid, 0.1 ml of isopropanol and 0.5 ml diethylether were added. After mixing and low speed centrifugation (2500×g, 5 min.) the organic layer was collected and dried under a stream of nitrogen. The resulting residue was dissolved in 0.1 ml sodium phosphate buffer pH 7.4, containing 0.1% bovine serum albumin. Samples were incubated overnight at 4° C. with the appropriate polyclonal antiserum, and $^3$H-labeled tracer (4000 cpm/tube) in a final volume of 0.3 ml. Unbound material was precipitated with 0.3 ml dextran-coated charcoal (Pharmacia, Sweden). After centrifugation at 4° C. aliquots of the supernatant (0.4 ml) were transferred to vials and after addition of scintillation liquid samples were counted in a Packard Tricarb scintillation counter. [$^3$H] Arachidonic acid (240 Ci/mmol) (New England Nuclear, Boston, Mass.) dissolved in isotonic $NaHCO_3$ (1.32% w/v) was injected through the uterine wall and the fontanellae into the embryonic brain. After injection fetuses were returned to the abdominal cavity for maintenance under physiological conditions. After 1 h, fetuses were delivered and immediately sacrificed. Cerebral hemispheres were rapidly excised for subsequent ex vivo incubation or for lipid extraction.

e) Results

Bilateral Permanent Cerebral Ischemia causes progressive loss of experimental animals up-to 6–7 days after surgery. As illustrated in FIG. 2, DP16 decreases post-ischemic mortality by 250%, compared with control using non-protected rats (p<0.01). These data demonstrate the potential ability of DP16 to treat otherwise fatal ischemic conditions.

f) Heart Ischemia-Langendorff Perfused Heart Model:

White rats were sacrificed by cervical dislocation and their hearts were rapidly removed and reperfused at 60 mmHg with modified Krebs-Henselleit buffer utilizing a Langendorff perfused heart model. Hearts were perfused for 10-min. preequlibration interval and were subsequently rendered either global ischemic (zero flow) or continuously perfused for the indicated time. Perfusion were terminated by rapid excision of ventricular tissue and directly submersion into cold homogenization buffer (10 mM imidazole, 10 mM KCl, 0.25 M sucrose [grade 1], pH 7.8) Both the activation of phospholipase A2 and its reversibility during reperfusion were temporally correlated to alterations in myocytic anaerobic metabolism and electron microscopic analyses.

g) Ventricular Fibrillation Model by Coronary Occlusion:

Dogs (11.6–20.7 kg) were anesthetized and connected to instrumentation to measure left circumflex coronary blood flow, left ventricular pressure, and ventricular electrogram. The left anterior descending artery was ligated and an anterior wall myocardial infarction was then produced. All leads to the cardiovascular instrumentation were tunneled under the skin to exit on the back of the animal's neck. Appropriate medicine was given to minimize postoperative pain and prevent inflammation. The ischemia test was performed after 3–4 weeks.

4.3) DP 16 Testing in Treatment of Epileptic Disorders:

a) Pilocarpine Based Model of Experimental Epilepsy:

Acetylcholine, acetylcholinesterase inhibitors and acetylcholine analogues are effective epileptogenic agents when applied intracerebrally or systematically (see ref. in Leite et al., Neurosci. & Biobeh. Rev., 1990, 14:511–17). It was demonstrated in different species that systemic administration of muscarinic cholinergic agonists produced electroencephalographic and behavioral limbic seizure accompanied by widespread brain damage resembling topographically that produced by kainic acid and folates and are frequently observed in autopsied human epileptics. Systemic injections of the pilocarpine, a potent muscarinic cholinergic agonist, are capable of producing a sequence of behavioral alterations including stirring spells, facial automatisms and motor limbic seizures, that develop over 1–2 hours and build progressively into limbic status and following by general status epilepticus.

b) Results

Immediately following injection of pilocarpine, akinesia, ataxic lurching, facial automatism and heart tremor dominated the animals' behavior. Further development of epileptic events is dose-dependent. Administration of pilocarpine in doses of 300–350 mg/kg causes appearance of limbic seizures with rearing, forelimb clonus, salivation, intense masticatory jaw movements and falling. Motor limbic seizures commenced after 20–30 min., recurred every 2–8 min and lead to status epilepticus. Increase of the dose of pilocarpine up-to 400 mg/kg abolished limbic seizures and after 15–25 min of initial behavioral alterations causes fatal general tonic-clonic convulsions. We consider this dose as the $LD_{100}$.

Administration of DP16 prior to pilocarpine prevented death in the animals and decreased epileptiform manifestations. As shown in FIG. 3, DP16 protected animals in a dose dependent fashion against generalized epileptic events induced by pilocarpine. As shown in FIG. 4, DP16 exhibits dose dependent therapeutic effects at doses in the range $10^{-8}$ to $10^{-5}$ mg/kg, and decreased the severity of the attacks as well, with a significant reduction in fatal seizures. For this particular model of epilepsy (pilocarpine 400 mg/kg; rats) the estimated therapeutic index (ET) of DP16 is 0.5 mg/kg/ $5\times10^{-7}$ mg/kg=$1\times10^6$. The data obtained suggest that DP16 is an extremely promising prodrug for the treatment of epileptic disorders.

c) Antiepileptic Effects of DP16:

Metrazol Minimal Seizures Test.

Figure 5:
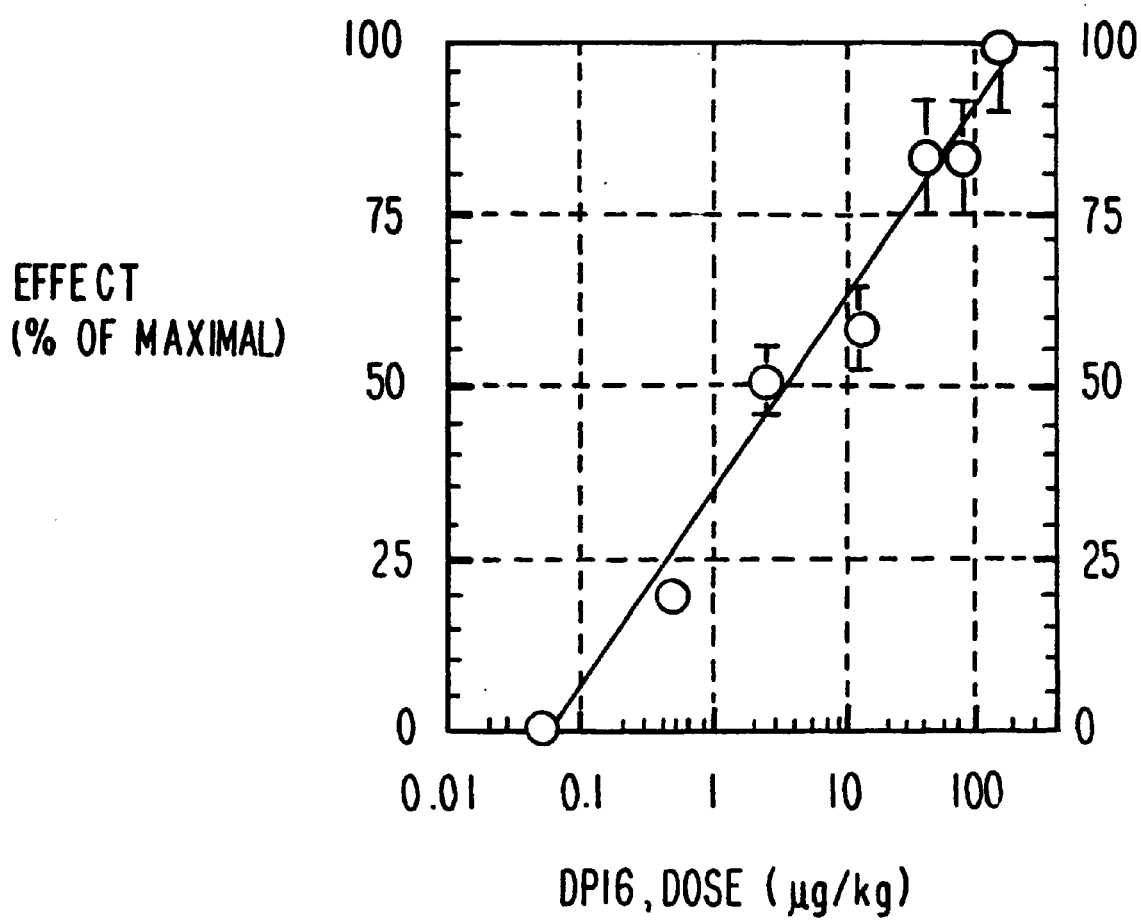
FIG. 5 illustrates the dose-response curve for protection afforded by DP16 in a metrazol minimum seizures test.

Testing of DP16 as a possible antiepileptic drug was performed on 3–4 week old male BALB/c mice (18–27 g). Animals were maintained on an adequate diet and allowed free access to food and water except briefly during the experimental period. Animals were separately housed for one hour in transparent plastic cages before treatment and during the experimental period. Drugs were dissolved in normal saline with injection volume adjusted to 0.01 ml/g of body weight. DP16 was administered i.p., in doses ranging from 0.1 to 300 µg/kg: (0.1 µg/kg: n=10, 5 µg/kg: n=10, 25 µg/kg: n=20, 75 µg/kg: n=20, 150 µg/kg: n=20, and 300 µg/kg: n=10 animals respectively). Control animals received injections i.p. of normal saline. DP16 or saline administration followed in 30 minutes by Metrazol (50 μg/kg, s.c.). Subsequently epileptic signs were observed for the next 30 minutes. Absence or relative delay of myoclonic jerks (MJ) in the experimental group was considered as indication of possible antiepileptic activity. Data were subjected to chi-square analysis with the computer statistic package "Stat-ViewII".

d) Results and Conclusions:

Metrazol in a dosage of 50 μg/kg, s.c. caused myoclonic jerks (MJ) in all of control mice with a latent period of 1011 min (n=11). The effect of DP16 on the appearance of minimal metrazol induced seizures is shown in FIG. 5. The doses are presented in this figure in terms of mg/kg of the active pharmacological component of the drug, i.e. BAPTA.

Mice treated with 0.1 μg/kg DP16 showed the same response to metrazol as control (untreated) animals. DP16 in doses ranging from 5 to 300 μg/kg exhibited a significant protective effect (p<0.001). The results of the test suggest a significant dose-dependent antiepileptic effect of DP16 on the metrazol induced seizures.

4.4) Investigation of Cardioprotective Effect of DP16:

a) Ex-vivo Rat Heart Low-flow—Reperfusion Model.

Method and Results

The following experiments demonstrate the protective effects of DP16 in models of cardiac diseases. Low-flow Reperfusion Langendorff's heart (Meely and Rovetto, 1975, METHODS IN ENZYMOLOGY, v39:43–60) is an established ex vivo model of a human ischemic heart. A severe decrease in perfusion pressure (PP) below 20 mm Hg (low-flow period) causes sinus bradycardia culminating by stable AV block ("AVB"; 10 out of 11 hearts) frequently followed by ventricular arythmia. Restoration of perfusion pressure causes paraxysmal tachyarrhythmia followed by irreversable ventricular fibrillation (VF).

The experiments were preformed ex vivo on 39 rat hearts. Heart electrical activity and perfusion pressure were stable following 15 min., each. Perfusion buffer was supplemented with DP16 (1.0 μg/l) following the stable AV block during low flow perfusion and during the Reperfusion period. Treatment of Cardiac Ischemia—Reperfusion with DP16.

The experimental protocol documented by FIG. 16 included peroiods of Normal Coronary Flow (FIG. 6, NF, panel 1) followed by Low-Flow (LF) and then by Normal flow-reperfusion (NF-Rp) (panels 2 and 3, respectively).

The experiments were performed by addition of DP16 (0.5–500 μg/l) to the perfusion buffer after AV block establishment. In 11 out of 16 experiments DP16 (1.0 μg/l) to the perfusion buffer caused complete restoration of AV synchronism and in the additional 5 cases it resulted in a decrease dlevel of AVB and prevented ventricular fibrillation (FIG. 6). Moreover, DP16 showed notable cardioprotective effects during the reperfusion period. Full restoration of the sinum rhythm was observed in 11 out of 16 experiments.

Conclusion

Evaluation of the cardioprotective effect of DP16 in the Low Flow-Reperfusion model as compared to treatment with parent compound BAPTA and to cell permeable BAPTA derivative, BAPTA-AM (supplied by Molecular Probes) and shown to have much better efficiency in resolving atrio-ventricular blockade and preventing ventricular fibrillation as indicated by FIG. 7.

b) DP16 Prevents Isoproterenol Induced Myocardial Damage

Method and Results

Administration of the potent β-adrenoreceptor agonist isoproterenol (ISO) is commonly accepted model of experimental myocardial pathology. The cardioprotective effect of DP16 was tested on 82 Sprague-Dawley female rats weighing 250–350 g. Myocardial damage was induced in rats by two consecutive injections of ISO (85 μg/kg, s.c.). When appropriate, the injections of ISO were followed in 30 and 180 minutes by DP16 (0.01 μg/kg, i.p.). The effect of DP16 was estimated by ECG analysis and determination of serum glutamate-oxaloacetate transaminase (SGOT) and lactatdehydrogenase (LDH) activity. Mortality of control rats after ISO intervention was 17.1±5.9% (7 out of 41). The surviving animals exhibited striking hyperacute deviation ST-segment in lead 1 and 2 ECG. Pathological signs on ECG were aggravated during the experimental period. In 48 hours after the second ISO injection all treated animals displayed pathological displacement of ST-segment. Administration of DP16 decreased mortality in 2 cases (2 out of 30). Animals receiving DP16 exhibited significantly (p<0.05) fewer alterations in the ECG. Pathological displacement of the ST-segment was found only on 28 and 40% of ECG (in 24 and in 48 hours following ISO respectively). Biochemical determination demonstrated a 1.7–1.9 fold increase if SGOT and LDH in ISO treated control rats (p<0.05). Treatment with DP16 substantially decreased the percentage of experimental animals exhibiting abnormal level of SGOT and LDH activity.

Conclusions

The data above suggest a significant cardioprotective effect of DP16 in an in vivo model of myocardial pathology.

c) Pilocarpine and Cardiotoxicity.

Two types of death were found in rats treated with pilocarpine: first death due to fatal convulsions and second, retarded death not immediately due to epileptic events. We attempted to understand the actual reason of retarded death of rats after pilocarpine-induced convulsions. Under macroscopic autopsy of these animals signs of cardiopulmonary damages were seen: lung edema and hemorrhages, dilated and in same cases deformed hearts. Dyeing of hearts with 0.1% Trypan blue in surviving animals revealed spotted picture of myocardia with areas of intensive dye absorption, i.e., damaged parts, and pale areas, i.e., infarctions. Thus, we can consider that after pilocarpine administration, there developed heart damage, which we term post-pilocarpine -seizure-cardiopathy (PSCP). Studies of PSCP in relation to DP16 evaluation were performed in vivo and in vitro with rats which survived after convulsive and sub-convulsive doses of Pilocarpine.

d) Post Seizure Cardiopathy (PSCP) Model:

Adult (2–3 months) male Sprague-Dawley rats were used for all experiments. They were fed with standard briquette chow with water ad libitum and were maintained in standard plastic cages (4–5 individuals in each cage) under natural illumination. A pilocarpine-scopolamine epileptic status model (pilocarpine) was performed as described earlier. In a group of 23 rats, pilocarpine was administered i.p. in different doses which ranged from 100 to 400 mg/kg body weight (B/W) for different periods of time; a second group of 17 rats was treated with DP16 prior to pilocarpine administration, wherein the DP16 was injected for 30 min before pilocarpine in the next dose range and its effect was investigated in the ensuing periods.

In vivo ECG (Birtcher-Cardio-Tracer, model 375, USA) in three standard leads were recorded under ketamine anesthesia (3.3 mg/kg Imalgene 100, Rhone Merieux, France and 7 mg/kg Rompun, Bayer Leverkusen, Germany, i.m.). ECG recordings were made in the period before pilocarpine injections (control), 24 h after pilocarpine administration (acute period) and after relative stabilization of cardiac function, on the 3–14th day after pilocarpine administration. Part of the ECG recordings were made under nembutal anesthesia (35 mg/kg, i.p.) in the period before establishing Langendorff's perfusion isolated heart preparation. Perfusion-Hypoxia-Reperfusion isolated heart model (PHR) was performed with the conventional Langendorff technique (non-recirculating perfusion system) adjusted to 37° C. in two modifications: 1. under constant Perfusion Pressure (PP)—60 mm Hg; or 2. under constant flow, established after the first 10–15 min perfusion with PP as above, by adjusting flow with help of peristaltic pump (Ismatec SA, Laboratoriumstechnic, Switzerland). In the case of constant PP the volume of effluent flow was measured on electron balance (Precisa 1000C-3000D, Switzerland). In case of constant flow, established at the control period, flow did not change during subsequent experimental periods and PP was recorded frequently. After 30 min of the control period, perfusion was stopped for 30 min and subsequent reperfusion period lasted 30 min. Direct ECG were recorded from ventricular apex (lead 1), auriculum (lead 2) and in-between (lead 3). The coronary vessells perfusion resistance (CVPR) was calculated in arbitrary units as follows: PP/flow/heart weight. Following the protocol above, hearts were subjected to perfusion with the dye Trypan blue (0.1%), in order to evaluate cellular damage and infarction.

e) Results and Discussion

ECG results in vivo demonstrated distinct ECG changes after pilocarpine injections in an acute stage of PSCP: statistically significant depressions of R- peak were noted under leads 1 and 2 (47% & 16% of control one respectively). DP16 treatment of PSCP normalized electrical activity at the acute stage in 5 out of 7 treated rats. It is known that the amplitude of ECG events are partly connected with the intensity of correspondent physiological processes. Thus, the pilocarpine-induced change of R-wave and its normalization by DP16 may reflect the ability of DP16 to cure ventricular weakness, at least under PSCP. Control rats display relative normalization of R-wave in 3–14 days after pilocarpine. However, R normalization apparently was correlated with drastically increased S-wave depth under lead 3 (36%) and lead 2 (61%). The last was not statistically significant in view of large variability. Increase of S-wave depth reflected damage typical of myocardial ischemia and possibly suggests infarction in Pilocarpine treated control animals. As during the acute stage of PSCP in the phase of stabilization, DP16 prevents the appearance of ECG alterations noted in control rats. The difference between animals protected with DP16 and those not protected, is statistically significant ($p<0.01$). In this period of PSCP there is marked elevation of Heart Rate in both control Pilocarpine, and in DP16 treated animals. Such tachycardia possibly is connected with hemodynamic insufficiency, which is characteristic for infarction pathophysiology. Thus, in vivo ECG investigation during long-term period after Pilocarpine injections revealed definite alteration of cardiac functions (PSCP), which in some animals may be cured by DP16-treatment.

f) Langendorff's Heart Model.

In the first 30 min of control, isolated Langendorff's hearts CVPR steadily increased and this elevation is statistically significant after 20 min. In all hearts, perfused after pilocarpine administration, initial perfusion flow was larger then in control, and subsequent CVPR significantly decreased. This decrease of coronary vessel tone was possibly connected with intracardial noradrenaline deficiency or paralysis, evoked by hypoxia.

Treatment of rats with DP16 prior to pilocarpine application prevents damage of CVPR regulation in both the initial and final periods of perfusion, thus providing evidence relating to the ability of DP16 to normalize coronary vessels function under hypoxic conditions. Cessation of perfusion for 30 min and subsequent reperfusion is characterized by the well-known broad class of cardiac damage events, which we classified with an arbitrary scale. Control hearts from non-treated control rats generally were restored after cessation of perfusion with distinct range of alterations (e.g., impaired myocardial excitability, conductivity and contractility). Mean point of recovery in control group is 6.3±0.6 (n=7). Hearts from pilocarpine-treated rats on different stages of PSCP demonstrated an increase of the spectrum and severity of pathological events, as the mean point of recovery was just 3.3±0.8, n=7, $p<0.05$. Recovery was frequently accompanied by ventricular fibrillation. Some of the hearts were not restored completely or restored atrial activity only. DP16 treatment prior to pilocarpine administrations increased ability of damaged hearts to restore after reperfusion cessation: the mean point was 6.4±0.6 (n=9). In this group of rats there was an increased incidence of cases of complete recovery. Thus, DP16 treatment of pilocarpine-induced heart damage (PSCP) produced a definite improvement in cardiac function.

4.5) General conclusions. The prodrug denoted DP16 exhibited significant therapeutic and protective effects in experimental models of stroke and ischemia as well as in models of epilepsy, comparable with using the corresponding drug in conventional form in an amount which is $10^5$–$10^6$ times the amount when used in the form of the prodrug of the invention.

Example 5

Preparation of Prodrug-3

"Prodrug-3" is the name used herein to denote a 1:1 ester of 1,2-bis-(2-aminophenoxy)ethane-N,N,N',N'-tetraacetic acid (BAPTA) with 1-myristylmyristyl alcohol and is prepared as follows. A solution of BAPTA (0.5 g, 1.05 mmol) in dimethylformamide (25 ml, freshly distilled over $CaH_2$), 1-myristylmyristyl alcohol (0.451 g, 1.1 mmol), N,N'-dicyclohexylcarbodiimide (0.216 g, 1.1 mmol) and 4-dimethylaminopyridine (0.025 g, 0.202 mmol) were stirred together for two days at room temperature under argon, in a 50 ml flask equipped with a magnetic stirrer. After two hours, N,N'-dicyclohexylurea began to precipitate. The reaction was monitored by TLC (90:10 v/v chloroform:methanol); $R_f$ of the product=0.62. The precipitate was removed by filtration and the filtrate was concentrated at 35° C. in vacuum. The residue was extracted with 25 ml of a 2:1:2 v/v mixture of chloroform:isopropanol:water. The organic layer was separated, washed with 1% aq. NaCl solution and dried over $Na_2SO_4$; it was then evaporated and the residue was passed through a 160×30 mm column of Kieselgel 60 (230–400 mesh ASTM), the desired product being eluted with a 90:10 v/v chloroform:methanol mixture. The 1-myristylmyristyl alcohol was prepared according to the method of Molotkovski, V. G. and Bergelson, L. D. (Biologicheska Chimia, 1982, 8(9): 1256–1262). The BAPTA-1-myristylmyristyl alcohol ester link in Prodrug-3 is susceptible to digestion by esterases.

Example 6

Preparation and Biological Properties of TVA16

"TVA16" is the name used herein to denote a 1:1 ester of valproic acid with the phosphorylcholine derivative $ROCH_2$—$CH(OH)$—$CH_2O$—$(PO_2)$—$OCH_2N^+(CH_3)_2$, where R is hexadecanoyl, and was prepared as follows. A solution of 1-hexadecanoyl-sn-glycero-3-phosphorylcholine (1.04 mmol) in chloroform (25 ml, freshly distilled over $P_2O_5$), valproic acid (0.159 g, 1.1 mmol), N,N'-dicyclohexylcarbodiimide (0.216 g, 1.1 mmol) and 4-dimethylaminopyridine (0.025 g, 0.202 mmol) were stirred together for two days at room temperature under argon, in a 50 ml flask equipped with a magnetic stirrer and glass beads (10 g, 5 mm diameter). After two hours, N,N'-dicyclohexylurea began to precipitate. The reaction was monitored by TLC (65:25:4 v/v chloroform:methanol:water); $R_f$ of the product=0.41. The precipitate and glass beads were removed by filtration and the filtrate was concentrated at 35° C. in vacuum. The residue was extracted with 25 ml of a 2:1:2 v/v mixture of chloroform:isopropanol:water. The organic layer was separated, washed with 1% aq. NaCl solution and dried over $Na_2SO_4$; it was then evaporated and the residue was passed through a 160×30 mm column of Kieselgel 60 (230–400 mesh ASTM), the desired product being eluted with a 65:25:4 v/v chloroform:methanol:water mixture; $R_f$=0.4.

A test sample of TVA16 was administered i.p. (0.01 to 100 mg/kg) to a group of three mice, one hour before an s.c. dose of metrazol (80 mg/kg). An effective dose was the amount which prevented convulsions (scored 2 points per animal) and/or death (scored 1 point per animal) in the subsequent 30 minutes. On this basis, the $ED_{100}$ could be calculated and is compared to known anticonvulsants in the following table.

TABLE 1

Anticonvulsant activity of known drugs and TVA16

| Compound | $ED_{100}$ (mg/kg) | Compound | $ED_{100}$ (mg/kg) |
|---|---|---|---|
| chlordiazepoxide | 25 | muscimol (i.p.) | 2.5 |
| diazepam | 2.5 | nifedipine | >100 |
| diphenylhydantoin | >100 | nimodipine | >300 |
| flunarizine | >300 | phenobarbital | 50 |
| glutethimide | 150 | sodium valproate | 500 |
| meprobamate | 200 | verapamil | >100 |
| MK-801 | 0.5 | TVA16 | 20 |

From the above data it may be seen that TVA16 has significant anticonvulsant activity and appears to be more than 500× as potent as sodium valproate.

FIG. 8 presents the dose response curves of valproic acid itself, in comparison to TVA, which clearly shows the improvement obtained with the prodrug according to the invention. The doses of each of the two drugs are calculated on the basis of mg of valproic acid administered per kg body weight of the animal.

Conclusion

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed:

1. A method for treating a disease or disorder in a mammal comprising administering to a mammal having a disease or disorder related to supranormal intracellular enzyme activity, an amount of a pharmaceutically acceptable prodrug effective to treat the disease or disorder, said prodrug comprising a pharmacologically active protein kinase inhibitor covalently bonded to an intracellular transporting adjuvant, said prodrug being cell membrane permeable and said covalent bond being cleaved in the presence of supranormal enzyme activity and cleavage of said covalent bond results in selective intracellular accumulation of therapeutic amounts of the pharmacologically active compound within cells having supranormal intracellular enzyme activity.

2. The method according to claim 1, wherein said prodrug is an ester of a protein kinase inhibitor carboxylic acid covalently bonded with a pharmaceutically acceptable alcohol selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$ alkyl esters of lysophosphatidic acids, lysoplasmalogens, lysophospholipids, lysophosphatidic acid amides, glycerophosphoric acids, lysophosphatidal ethanolamine, lysophosphatidyl ethanolamine, N-mono-($C_{1-4}$)-alkyl and N,N-di-($C_{1-4}$)-alkyl and quaternary derivatives of the amines thereof.

3. The method according to claim 2, wherein the protein kinase inhibitor is protein kinase inhibitor K252b from Nocardiopsis sp.

4. The method according to claim 1 wherein the protein kinase inhibitor contains an amine group with a replaceable N-linked hydrogen atom, and the prodrug is an amide thereof with a phosphoric acid derivative selected from the group consisting of glycerophosphoric acids, O-acylglycerophosphoric acids, etherified glycerophosphoric acids, and monoacylated monoetherified glycerophosphoric acids.

5. The method according to claim 1, wherein the protein kinase inhibitor is isoquinoline-5-sulfonamide which is N-substituted by an acyclic or heterocyclic aminoalkyl radical.

6. The method according to claim 5, wherein said aminoalkyl radical is selected from the group consisting of $NHCH_2CH_2NHCH_3$ and 2-methylpiperazin-1-yl.

7. The method according to claim 1, wherein the protein kinase inhibitor contains at least one phenolic hydroxy group, and the prodrug is an ester thereof with a phosphoric acid derivative selected from the group consisting of glycerophosphoric acids, O-acylglycerophosphoric acids, etherified glycerophosphoric acids, and monoacylated monoetherified glycerophosphoric acids.

8. The method according to claim 1, wherein the protein kinase inhibitor is 4',5,7-trihydroxyisoflavone.

9. The method according to claim 1, wherein the prodrug is administered by a route selected from the group consisting of intramuscular injection, intravenous injection, infusion into a body cavity, cerebrospinal injection, localized infiltration of a target tissue, buccal absorption and aerosol inhalation in an amount effective to treat said disease or disorder.

10. The method according to claim 1, wherein said disease or disorder is selected from the group consisting of localized tissue ischemia, stroke, epilepsy, asthma and allergy.

11. A pharmaceutically acceptable prodrug comprising a pharmacologically active compound covalently bonded to an intracellular transporting adjuvant, said pharmacologically active compound being effective to treat a disease or disorder related to supranormal enzyme activity, said covalent bond being cleaved in the presence of supranormal intracellular enzyme activity and said prodrug being pharmacologically inactive prior to cleavage.

12. A prodrug according to claim 11, wherein said pharmacologically active compound is a pharmacologically active carboxylic acid and said intracellular transporting adjuvant comprises at least one pharmaceutically acceptable alcohol which is selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lysoplasmalogens, lysophospho-lipids, lysophosphatidic acid amides, glycerophosphoric acids, lysophophatidalethanolamine, lysophosphatidyl-ethanolamine, N-mono-($C_{1-4}$)-alkyl and N,N-di-($C_{1-4}$)-alkyl and quaternary derivatives of the amines thereof.

13. A prodrug according to claim 12, wherein said pharmacologically active carboxylic acid is selected from branched-chain aliphatic carboxylic acids, salicylic acids, steroidal carboxylic acids, monoheterocyclic carboxylic acids and polyheterocyclic carboxylic acids.

14. A prodrug according to claim 11, wherein the pharmacologically active compound is a protein kinase inhibitor.

15. A prodrug according to claim 14, which is an ester of a protein kinase inhibitor carboxylic acid covalently bonded with a pharmaceutically acceptable alcohol selected from the group consisting of glycerol, $C_{3-20}$ fatty acid-monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lyso-phosphatidic acids, lysoplasmalogens, lysophospholipids, lysophosphatidic acid amides, glycerophosphoric acids, lysophophatidal-ethanolamine, lysophosphatidyl-ethanolamine, N-mono-($C_{1-4}$)-alkyl and N,N-di-($C_{1-4}$)-alkyl and quaternary derivatives of the amines thereof.

16. A prodrug according to claim 15, wherein the protein kinase inhibitor is protein kinase inhibitor K252b from Nocardiopsis sp.

17. A prodrug according to claim 14, wherein the protein kinase inhibitor contains an amine group with a replaceable N-linked hydrogen atom, and the prodrug is an amide thereof with a phosphoric acid derivative selected from the group consisting of glycerophosphoric acids, O-acylglycerophosphoric acids, etherified glycerophosphoric acids, and monoacylated monoetherified glycerophosphoric acids.

18. A prodrug according to claim 17, wherein the protein kinase inhibitor is isoquinoline-5-sulfonamide which is N-substituted by a radical selected from the group consisting of an acyclic aminoalkyl and a heterocyclic aminoalkyl radical.

19. A prodrug according to claim 18, wherein said aminoalkyl radical is selected from the group consisting of $NHCH_2CH_2NHCH_3$ and 2-methylpiperazin-1-yl.

20. A prodrug according to claim 14, wherein the protein kinase inhibitor contains at least one phenolic hydroxy group, and the prodrug is an ester thereof with a phosphoric acid derivative selected from the group consisting of glycerophosphoric acids, O-acyl-glycerophosphoric acids, etherified glycerophosphoric acids, and monoacylated monoetherified glycerophosphoric acids.

21. A prodrug according to claim 20, wherein the protein kinase inhibitor is 4',5,7-trihydroxyisoflavone.

* * * * *